(12) United States Patent
Sommer et al.

(10) Patent No.: US 8,538,523 B2
(45) Date of Patent: *Sep. 17, 2013

(54) EVALUATING THERAPEUTIC STIMULATION ELECTRODE CONFIGURATIONS BASED ON PHYSIOLOGICAL RESPONSES

(75) Inventors: John L. Sommer, Coon Rapids, MN (US); David Wayne Bourn, Maple Grove, MN (US); Mark T. Marshall, Forest Lake, MN (US); Michael D. Eggen, Lake Elmo, MN (US); Gabriela C. Miyazawa, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/616,300

(22) Filed: Sep. 14, 2012

(65) Prior Publication Data
US 2013/0006332 A1   Jan. 3, 2013

Related U.S. Application Data

(63) Continuation of application No. 12/195,317, filed on Aug. 20, 2008, now Pat. No. 8,326,418.

(60) Provisional application No. 60/956,832, filed on Aug. 20, 2007, provisional application No. 60/956,868, filed on Aug. 20, 2007, provisional application No. 61/049,245, filed on Apr. 30, 2008.

(51) Int. Cl.
*A61N 1/365* (2006.01)

(52) U.S. Cl.
USPC .................. 607/9; 607/15; 607/17; 607/18

(58) Field of Classification Search
USPC .......................................... 607/9, 15, 17, 18
See application file for complete search history.

(56) References Cited

U.S. PATENT DOCUMENTS

| | | | |
|---|---|---|---|
| 3,757,792 | A | 9/1973 | Muller et al. |
| 4,106,512 | A | 8/1978 | Bisping |

(Continued)

FOREIGN PATENT DOCUMENTS

| | | |
|---|---|---|
| EP | 0 769 308 A1 | 4/1997 |
| EP | 1 127 587 A2 | 8/2001 |

(Continued)

OTHER PUBLICATIONS

U.S. Appl. No. 12/195,277, filed Aug. 20, 2008, entitled Electrode Configurations for Directional Leads by Bourn et al.
U.S. Appl. No. 12/195,287, filed Aug. 20, 2008, entitled Implantable Medical Lead With Biased Electrode by Eggen et al.
U.S. Appl. No. 12/195,313, filed Aug. 20, 2008, entitled Stimulation Filed Management by Eggen et al.

(Continued)

*Primary Examiner* — Joseph Dietrich
(74) *Attorney, Agent, or Firm* — Reed A. Duthler

(57) ABSTRACT

A medical system comprises a plurality of electrodes; at least one sensor configured to output at least one signal based on at least one physiological parameter of a patient; and a processor. The processor is configured to control delivery of stimulation to the patient using a plurality of electrode configurations. Each of the electrode configurations comprises at least one of the plurality of electrodes. For each of the electrode configurations, the processor is configured to determine a first response of target tissue to the stimulation based on the signals, and a second response of non-target tissue to the stimulation based on the signals. The processor is also configured to select at least one of the electrode configurations for delivery of stimulation to the patient based on the first and second responses for the electrode configurations. As examples, the target tissue may be a left ventricle or vagus nerve.

16 Claims, 11 Drawing Sheets

(56) References Cited

U.S. PATENT DOCUMENTS

| | | |
|---|---|---|
| 4,217,913 A | 8/1980 | Dutcher |
| 4,390,023 A | 6/1983 | Rise |
| 4,660,571 A | 4/1987 | Hess et al. |
| 4,662,382 A | 5/1987 | Sluetz et al. |
| 4,711,251 A | 12/1987 | Stokes |
| 4,819,647 A | 4/1989 | Byers et al. |
| 4,922,607 A | 5/1990 | Doan et al. |
| 4,946,457 A | 8/1990 | Elliott |
| 4,961,434 A | 10/1990 | Stypulkowski |
| 5,000,194 A | 3/1991 | van den Honert et al. |
| 5,029,585 A | 7/1991 | Lieber et al. |
| 5,037,497 A | 8/1991 | Stypulkowski |
| 5,117,824 A | 6/1992 | Keimel et al. |
| 5,246,014 A | 9/1993 | Williams et al. |
| 5,324,310 A | 6/1994 | Greeninger et al. |
| 5,431,693 A | 7/1995 | Schroeppel |
| 5,462,545 A | 10/1995 | Wang et al. |
| 5,522,874 A | 6/1996 | Gates |
| 5,531,779 A | 7/1996 | Dahl et al. |
| 5,534,018 A | 7/1996 | Wahlstrand et al. |
| 5,584,873 A | 12/1996 | Shoberg et al. |
| 5,601,615 A | 2/1997 | Markowitz et al. |
| 5,643,330 A | 7/1997 | Holsheimer et al. |
| 5,662,699 A | 9/1997 | Hamedi et al. |
| 5,683,431 A | 11/1997 | Wang |
| 5,741,214 A | 4/1998 | Ouchi et al. |
| 5,755,664 A | 5/1998 | Rubenstein |
| 5,755,766 A | 5/1998 | Chastain et al. |
| 5,772,108 A | 6/1998 | Ruggiere, Sr. et al. |
| 5,775,331 A | 7/1998 | Raymond et al. |
| 5,800,465 A | 9/1998 | Thompson et al. |
| 5,824,030 A | 10/1998 | Yang et al. |
| 5,836,875 A | 11/1998 | Webster, Jr. |
| 5,843,148 A | 12/1998 | Gijsbers et al. |
| 5,861,012 A | 1/1999 | Stroebel |
| 5,895,416 A | 4/1999 | Barreras, Sr. et al. |
| 5,916,158 A | 6/1999 | Webster, Jr. |
| 5,941,906 A | 8/1999 | Barreras, Sr. et al. |
| 5,983,126 A | 11/1999 | Wittkampf |
| 5,987,746 A | 11/1999 | Williams |
| 6,052,624 A | 4/2000 | Mann |
| 6,064,905 A | 5/2000 | Webster, Jr. et al. |
| 6,071,279 A | 6/2000 | Whayne et al. |
| 6,078,830 A | 6/2000 | Levine et al. |
| 6,085,118 A | 7/2000 | Hirschberg et al. |
| 6,146,379 A | 11/2000 | Fleischman et al. |
| 6,161,029 A | 12/2000 | Spreigl et al. |
| 6,205,360 B1 | 3/2001 | Carter et al. |
| 6,263,250 B1 | 7/2001 | Skinner |
| 6,317,633 B1 | 11/2001 | Jorgenson et al. |
| 6,381,496 B1 | 4/2002 | Meadows et al. |
| 6,393,325 B1 | 5/2002 | Mann et al. |
| 6,430,425 B1 | 8/2002 | Bisping |
| 6,456,876 B1 | 9/2002 | Kroll |
| 6,510,347 B2 | 1/2003 | Borkan |
| 6,609,032 B1 | 8/2003 | Woods et al. |
| 6,643,546 B2 | 11/2003 | Mathis et al. |
| 6,740,082 B2 | 5/2004 | Shadduck |
| 6,839,588 B1 | 1/2005 | Rudy |
| 6,978,178 B2 | 12/2005 | Sommer et al. |
| 6,999,819 B2 | 2/2006 | Swoyer et al. |
| 7,047,084 B2 | 5/2006 | Erickson et al. |
| 7,162,299 B1 | 1/2007 | Kroll et al. |
| 7,214,189 B2 | 5/2007 | Zdeblick |
| 7,269,457 B2 | 9/2007 | Shafer et al. |
| 7,295,875 B2 | 11/2007 | Wallace et al. |
| 7,366,573 B2 | 4/2008 | Knapp et al. |
| 2002/0183817 A1 | 12/2002 | Van Venrooij et al. |
| 2002/0193834 A1 | 12/2002 | Levine |
| 2003/0065365 A1 | 4/2003 | Zhu et al. |
| 2003/0078623 A1 | 4/2003 | Weinberg et al. |
| 2003/0083724 A1 | 5/2003 | Jog et al. |
| 2003/0204232 A1 | 10/2003 | Sommer et al. |
| 2003/0220676 A1 | 11/2003 | Helland |
| 2003/0236558 A1 | 12/2003 | Whitehurst et al. |
| 2004/0034394 A1 | 2/2004 | Woods et al. |
| 2004/0088015 A1 | 5/2004 | Casavant et al. |
| 2004/0098074 A1 | 5/2004 | Erickson et al. |
| 2004/0167583 A1 | 8/2004 | Knudson et al. |
| 2004/0172088 A1 | 9/2004 | Knudson et al. |
| 2004/0193021 A1 | 9/2004 | Zdeblick et al. |
| 2004/0193240 A1 | 9/2004 | Michel |
| 2004/0260310 A1 | 12/2004 | Harris |
| 2004/0267328 A1 | 12/2004 | Duffin et al. |
| 2005/0038481 A1 | 2/2005 | Chinchoy et al. |
| 2005/0038489 A1 | 2/2005 | Grill |
| 2005/0131486 A1 | 6/2005 | Boveja et al. |
| 2005/0131506 A1 | 6/2005 | Rezai et al. |
| 2005/0137644 A1 | 6/2005 | Boveja et al. |
| 2005/0143787 A1 | 6/2005 | Boveja et al. |
| 2005/0171587 A1 | 8/2005 | Daglow et al. |
| 2006/0058588 A1 | 3/2006 | Zdeblick et al. |
| 2006/0168805 A1 | 8/2006 | Hegland et al. |
| 2006/0173262 A1 | 8/2006 | Hegland et al. |
| 2006/0206158 A1 | 9/2006 | Wu et al. |
| 2006/0241711 A1 | 10/2006 | Sathaye |
| 2006/0247688 A1 | 11/2006 | Olson et al. |
| 2007/0055124 A1 | 3/2007 | Viswanathan et al. |
| 2007/0112401 A1 | 5/2007 | Balachandran et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0179579 A1 | 8/2007 | Feler et al. |
| 2007/0203537 A1 | 8/2007 | Goetz et al. |
| 2007/0203540 A1 | 8/2007 | Goetz et al. |
| 2007/0203541 A1 | 8/2007 | Goetz et al. |
| 2007/0203542 A1 | 8/2007 | Goetz et al. |
| 2007/0203544 A1 | 8/2007 | Goetz et al. |
| 2007/0203546 A1 | 8/2007 | Stone et al. |
| 2008/0077186 A1 | 3/2008 | Thompson et al. |
| 2008/0097566 A1 | 4/2008 | Colliou |
| 2008/0255647 A1 | 10/2008 | Jensen et al. |

FOREIGN PATENT DOCUMENTS

| | | |
|---|---|---|
| EP | 1 438 984 A2 | 7/2004 |
| WO | WO 01/03767 | 1/2001 |
| WO | WO 01/74441 | 10/2001 |
| WO | WO 02/068042 | 9/2002 |
| WO | WO 2006/029090 | 3/2006 |
| WO | WO 2006/042039 | 4/2006 |
| WO | WO 2006/069322 | 6/2006 |
| WO | WO 2006/069323 | 6/2006 |
| WO | WO 2008/094879 | 8/2008 |

OTHER PUBLICATIONS

International Report on Patentability from international application No. PCT/US2008/009906, dated Feb. 24, 2010, 5 pp.

International Search Report and Written Opinion from corresponding PCT Application Serial No. PCT/US2008/009906 mailed Jun. 9, 2009 (10 pages).

Response to Office Action dated Aug. 17, 2011, from U.S. Appl. No. 12/195,287, filed Nov. 17, 2011, 8 pp.

Response to Office Action dated Jan. 4, 2012, from U.S. Appl. No. 12/195,287, filed Feb. 23, 2012, 12 pp.

Office Action from U.S. Appl. No. 12/195,287, dated Mar. 15, 2012, 9 pp.

Office Action from U.S. Appl. No. 12/195,287, dated Jan. 4, 2012, 9 pp.

Office Action from U.S. Appl. No. 12/195,287, dated Aug. 17, 2011, 10 pp.

Office Action from U.S. Appl. No. 12/195,287, dated Mar. 17, 2011, 8 pp.

Response to Office Action dated Mar. 17, 2011, from U.S. Appl. No. 12/195,287, filed May 20, 2011, 7 pp.

Office Action from U.S. Appl. No. 12/195,313, dated Jan. 25, 2011, 6 pp.

Office Action from U.S. Appl. No. 12/195,277, dated Mar. 14, 2011, 17 pp.

EVALUATING THERAPEUTIC STIMULATION ELECTRODE CONFIGURATIONS BASED ON PHYSIOLOGICAL RESPONSES

RELATED APPLICATION

This application is a continuation of U.S. patent application Ser. No. 12/195,317, filed Aug. 20, 2008, entitled "EVALUATIONG THERAPEUTIC STIMULATION ELECTRODE CONFIGURATIONS BASED ON PHYSIOLOGICAL RESPONSES", herein incorporated by reference in its entirety.

In addition, this application claims the benefit of U.S. Provisional Application No. 60/956,832, filed Aug. 20, 2007, U.S. Provisional Application No. 60/956,868, filed Aug. 20, 2007 and U.S. Provisional Application No. 61/049,245, filed Apr. 30, 2008 each of which are hereby incorporated by reference.

TECHNICAL FIELD

The present disclosure relates to medical devices, more particularly to programming a medical device to deliver therapy.

BACKGROUND

In the medical field, a wide variety of medical devices use implantable leads. For example, implantable cardiac pacemakers provide therapeutic stimulation to the heart by delivering pacing, cardioversion, or defibrillation pulses via implantable leads. Implantable cardiac pacemakers deliver such pulses to the heart via electrodes disposed on the leads, e.g., near distal ends of the leads. Implantable medical leads may be configured to allow electrodes to be positioned at desired cardiac locations so that the pacemaker can deliver pulses to the desired locations.

Implantable medical leads are also used with other types of stimulators to provide, as examples, neurostimulation, muscular stimulation, or gastric stimulation to target patient tissue locations via electrodes on the leads and located within or proximate to the target tissue. As one example, at least one implantable medical lead may be positioned proximate to the vagus nerve for delivery of neurostimulation to the vagus nerve. Additionally, implantable medical leads may be used by medical devices for patient sensing and, in some cases, for both sensing and stimulation. For example, electrodes on implantable medical leads may detect electrical signals within a patient, such as an electrocardiogram, in addition to delivering electrical stimulation.

For delivery of cardiac pacing pulses to the left ventricle (LV), an implantable medical lead is typically placed through the coronary sinus and into a coronary vein. However, when located in the coronary sinus or a coronary vein, an LV lead may also be located near the phrenic nerve. Phrenic nerve stimulation is generally undesirable during LV pacing therapy. In some instances, the implantable lead may need to be specifically positioned to avoid phrenic nerve stimulation during LV pacing therapy, which may result in placing the electrodes of the LV lead at a non-optimal site for LV pacing.

In some cases, implantable medical leads with ring electrodes are used as an alternative to cuff electrodes for delivery of neurostimulation to the vagus nerve. However, when located near the vagus nerve, the implantable medical lead may also be located near neck muscles. Stimulation of neck muscles is generally undesirable during therapeutic vagal neurostimulation.

SUMMARY OF THE DISCLOSURE

Implantable medical leads including a plurality of electrodes may provide stimulation therapy using a multitude of electrode configurations. For example, individual electrodes can be configured as anodes or cathodes and any combination of anode and cathode electrodes may be used. In addition, any of the electrodes may be used as unipolar electrodes. As another example, a housing of an implantable medical device may also be selected as an anode or cathode in combination with any selected electrode configuration. Different electrode configurations may direct stimulation fields to different locations such as different tissues within a patient.

For any given patient and stimulation therapy, determining at least one preferred electrode configuration may require a significant amount of trial and error to determine the efficacy a plurality of potential electrode configuration. In addition, for a given set of electrodes, determining a patient's physiological responses can be difficult. The techniques disclosed herein may be useful to simplify the selection at least one preferred electrode configuration and determination of a patient's physiological responses to stimulation therapy including physiological response(s) to stimulation therapy resulting from a stimulation field interaction with target tissue and non-target tissue of a patient.

A physiological response(s) associated with stimulation field interaction with target tissue may be evaluated according to desired patient response(s) to the stimulation therapy, e.g., the effectiveness or efficacy of the stimulation therapy for an electrode configuration including current and/or voltage amplitudes for the electrodes included in the electrode configuration. Similarly, a physiological response(s) associated with stimulation field interaction with non-target tissue may be evaluated according to unbeneficial patient response(s) to the stimulation therapy, e.g., unwanted side-effect(s) attributable to the stimulation therapy. The physiological response(s) associated with stimulation field interactions with target tissue and non-target tissue for multiple electrode configurations may be objectively compared to determine preferable electrode configurations or even a most preferred electrode configuration for continued stimulation therapy. Examples of physiological response(s) include generally desired changes of the function of the heart, such as changes in contractility of a heart, cardiac output, electrocardiogram (ECG) morphology, heart rate, intercardiac pressure and a time derivative of intercardiac pressure (dP/dt).

One example of a physiological response is a capture threshold that produces a desired patient response to the stimulation therapy. As referred to herein, a capture threshold refers to a therapy parameter used in the therapy directed to the target tissue. As examples, the target tissue may be a left ventricle or vagus nerve of a patient. For example, a capture threshold may be a stimulation voltage amplitude, stimulation current amplitude, stimulation waveform, stimulation pulse width, stimulation pulse frequency, other therapy parameter or a combination of therapy parameters that produces desired patient response(s) to the stimulation therapy.

In one example, the disclosure provides a medical system comprising a plurality of electrodes; at least one sensor configured to output at least one signal based on at least one physiological parameter of a patient; and a processor. The processor is configured to control delivery of stimulation to the patient using a plurality of electrode configurations. Each of the electrode configurations comprises at least one of the plurality of electrodes. For each of the electrode configurations, the processor is also configured to determine a first response of target tissue to the stimulation based on the signals, and a second response of non-target tissue to the stimulation based on the signals. The processor is also configured to select at least one of the electrode configurations for delivery of stimulation to the patient based on the first and second responses s for the electrode configurations.

In another example, the disclosure provides a method for evaluating therapeutic stimulation of a plurality of electrode configurations comprising controlling delivery of stimulation to a patient using the plurality of electrode configurations; for each of the electrode configurations, determining a first response of target tissue to the stimulation and a second response of non-target tissue to the stimulation based on at least one sensor signal, wherein the sensor signals are based on at least one physiological parameter of the patient; and selecting at least one of the electrode configurations for delivery of stimulation to the patient based on the first and second responses for the electrode configurations.

In an example, the disclosure provides a computer-readable medium comprising instructions that cause a programmable processor to control delivery of stimulation to a patient using a plurality of electrode configurations; for each of the electrode configurations, determine a first response of target tissue to the stimulation and a second response of non-target tissue to the stimulation based on at least one sensor signal, wherein the sensor signals are based on at least one physiological parameter of the patient; and select at least one of the electrode configurations for delivery of stimulation to the patient based on the first and second responses for the electrode configurations.

In another example, the disclosure provides a medical device comprising a means for delivering stimulation therapy to a patient using a plurality of electrode configurations; and a means for evaluating the relative suitability of the of the electrode configurations for delivering stimulation therapy to target tissue of the patient.

The details of the present disclosure are set forth in the accompanying drawings and the description below. Other features, objects, and benefits of the present disclosure will be apparent from the description and drawings, and from the claims.

DETAILED DESCRIPTION

While the description primarily refers to implantable electrical stimulation leads and implantable medical devices that deliver stimulation therapy to a patient's heart, e.g., pacemakers, and pacemaker-cardioverter-defibrillators, the features and techniques described herein are useful in other types of medical device systems, which may include other types of implantable medical leads and implantable medical devices. For example, the features and techniques described herein may be used in systems with medical devices that deliver neurostimulation to the vagal nerve. As other examples, the features and techniques described herein may be embodied in systems that deliver other types of neurostimulation therapy (e.g., spinal cord stimulation or deep brain stimulation), stimulation of at least one muscle or muscle groups, stimulation of at least one organ such as gastric system stimulation, stimulation concomitant to gene therapy, and, in general, stimulation of any tissue of a patient.

In addition, while the examples shown in the figures include leads coupled at their proximal ends to a stimulation therapy controller, e.g., implantable medical device, located remotely from the electrodes, other configurations are also possible and contemplated. In some examples, a lead comprises a portion of a housing, or a member coupled to a housing, of stimulation generator located proximate to or at the stimulation site, e.g., a microstimulator. In other examples, a lead comprises a member at stimulation site that is wirelessly coupled to an implanted or external stimulation controller or generator. For this reason, as referred to herein, the term of a "lead" includes any structure having at least one stimulation electrode disposed on its surface.

Figure 1:
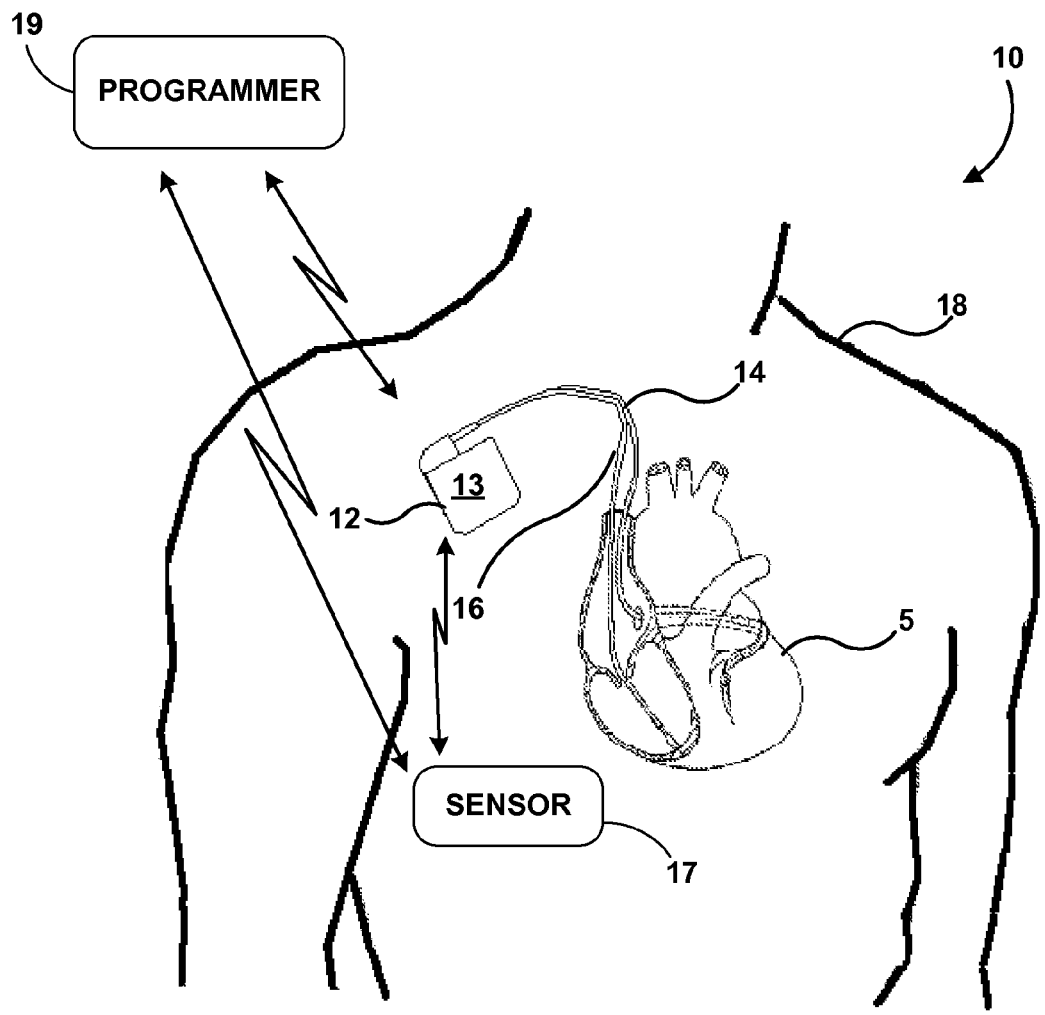
FIG. 1 is a conceptual diagram illustrating an example implantable medical device system.

FIG. 1 is a conceptual diagram illustrating an example implantable medical system 10 comprising an implantable medical device (IMD) 12, and implantable medical leads 14, 16 electrically coupled to IMD 12. In the embodiment shown in FIG. 1, system 10 is implanted within a patient 18 to deliver electrical stimulation therapy to the heart 5 of patient 18. Patient 18 ordinarily, but not necessarily, will be a human patient.

In the embodiment shown in FIG. 1, IMD 12 is a cardiac pacemaker, cardioverter, defibrillator, or pacemaker-cardioverter-defibrillator (PCD) that generates therapeutic electrical stimulation for pacing, cardioversion or defibrillation, which may take the form of pulses or continuous time signals. Leads 14, 16 each include at least one electrode that are each positioned within (e.g., intravenously) or proximate to (e.g., epicardially) heart 5 in order to deliver the therapeutic electrical stimulation from IMD 12 to heart 5. In some embodiments, at least one of leads 14, 16 may provide stimulation to heart 5 without contacting heart 5, e.g., at least one of leads 14, 16 may include a subcutaneous electrode.

In the illustrated embodiment, a distal end of lead 14 is positioned proximate to the left ventricle (LV) of patient 18 and, more particularly, within the coronary sinus or a coronary vein accessed via the coronary sinus. In the illustrated embodiment, lead 14 is configured for intravenous introduction into heart 5. For example, lead 14 may have a lead body diameter of between 0.020 inches and 0.100 inches. A distal end of lead 16 is positioned within the right ventricle of patient 18. Accordingly, in the illustrated example, lead 14 may be referred to as a left ventricular (LV) lead, and lead 16 may be referred to as a right ventricular (RV) lead. IMD 12 may deliver coordinated pacing signals to heart 5 via leads 14 and 16 to, for example, to resynchronize the action of the left and right ventricles.

When lead 14 is positioned within the coronary sinus or a coronary vein, lead 14 may be proximate to the phrenic nerve. This positioning may result in unintentional phrenic nerve stimulation, which is generally undesirable during LV pacing therapy. For example, phrenic nerve stimulation may cause a hiccup each time a stimulation signal is delivered to stimulate LV contraction, e.g., with each heart beat. It may be desirable to selectively stimulate the myocardium of the LV of heart 5 without stimulating the phrenic nerve. Accordingly, as described in further detail below, at least one electrode configuration of lead 14 may be evaluated to assess physiological response(s) associated with stimulation field interaction with a patient's myocardial and phrenic nerves. Evaluation of physiological response(s) associated with stimulation field interaction with a patient's myocardial and phrenic nerves may help guide selection of an electrode configuration that selectively stimulates the LV without stimulating the phrenic nerve.

As another example, lead 14 may be positioned within the internal jugular vein for vagus nerve stimulation. Consequently, lead 14 may be positioned proximate to the neck muscles of patient 18. Stimulation of the muscle tissue of the neck may cause undesirable muscle contraction. Therefore, it may be desirable to selectively stimulate the vagus nerve without stimulating the muscle tissue proximate to the vagus nerve. At least one electrode configuration of lead 14 may be evaluated to assess physiological response(s) associated with stimulation field interaction with a patient's vagus nerve and neck muscles. Evaluation of physiological response(s) associated with stimulation field interaction with a patient's vagus nerve and neck muscles may help guide selection of an electrode configuration that selectively stimulates the vagus nerve without stimulating the neck muscles.

As previously mentioned, leads including the features described herein may be used to deliver neurostimulation therapy from a medical device to target neural tissues of a patient, such as the vagal nerve. Furthermore, although described herein as being coupled to IMDs, implantable medical leads may also be percutaneously coupled to an external medical device for deliver of electrical stimulation to target locations within the patient.

As shown in FIG. 1, system 10 may also include a programmer 19, which may be a handheld device, portable computer, or workstation that provides a user interface to a clinician or other user. The clinician may interact with the user interface to program stimulation parameters for IMD 12, which may include, for example, the electrodes of leads 14, 16 that are activated, the polarity of each of the activated electrodes, a current or voltage amplitude for each of the activated electrodes and, in the case of stimulation in the form of electrical pulses, pulse width and pulse rate (or frequency) for stimulation signals to be delivered to patient 18. As referred to herein, an amplitude of stimulation therapy may be characterized as a magnitude of a time varying waveform. For example, an amplitude of stimulation therapy may be measured in terms of voltage (volts), current (ampere), or electric field (volts/meter). Typically, amplitude is expressed in terms of a peak, peak to peak, or root mean squared (rms) value. The clinician may also interact with the user interface to program escape intervals, rate response parameters, or any other stimulation parameters known for use in controlling cardiac pacing, or other types of therapeutic stimulation.

Programmer 19 supports telemetry (e.g., radio frequency telemetry) with IMD 12 to download stimulation parameters and, optionally, upload operational or physiological data stored by IMD 12. In this manner, the clinician may periodically interrogate IMD 12 to evaluate efficacy and, if necessary, modify the stimulation parameters. IMD 12 and programmer 19 may communicate via cables or a wireless communication, as shown in FIG. 1. Programmer 19 may, for example, communicate via wireless communication with IMD 12 using RF telemetry techniques known in the art.

In some embodiments, at least one of the electrodes of leads 14, 16, or one or more different leads, may include at least one sense electrode or sensor that senses a physiological parameter of patient 12, such as, but not limited to, electrocardiogram (ECG) parameters, a heart rate, QRS width, atrioventricular (AV) Dissociation, respiration rate, respiratory volume, core temperature, diaphragmatic stimulation such as hiccups, skeletal muscle activity, blood oxygen level, cardiac output, blood pressure, intercardiac pressure, time derivative of intercardiac pressure (dP/dt), electromyogram (EMG) parameters, or electroencephalogram (EEG) parameters. Sense electrodes may be the same electrodes used for delivery of electrical stimulation to patient 18, or different electrodes. Therapy system 10 may also include at least one sensor 17 in addition to or instead of sense electrodes and sensors on the leads 14, 16. Sensor 17 may be configured to detect an activity level, motion, posture, intracardiac, intravascular or other pressure within the patient, or another physiological parameter of patient 18. For example, sensor 17 may comprise an accelerometer. Sensor 17 may generate a signal that varies as a function of at least one physiological parameter of patient 18.

Sensor 17 may be implanted within or external to patient 18, and may be wirelessly coupled to IMD 12 or coupled to IMD 12 via a lead, such as leads 14, 16 or another lead. For example, sensor 17 may be implanted within patient 18 at a different site than IMD 12 or sensor 17 may be external. As one example sensor 17 may include an accelerometer useful to detect, e.g., the presence of cardiac pulse, diaphragmatic stimulation such as hiccups and/or skeletal muscle activity. In some examples, sensor 17 may be located on or within a housing of IMD 12. In addition or instead of being coupled to IMD 12, in some cases, sensor 17 may be wirelessly coupled to programmer 19 or coupled to programmer 19 by a wired connection. As used herein, the term "sensor" refers to at least one electrode, or any other sensor, that provides a signal that varies as a function of a sensed physiological parameter.

Figure 2:
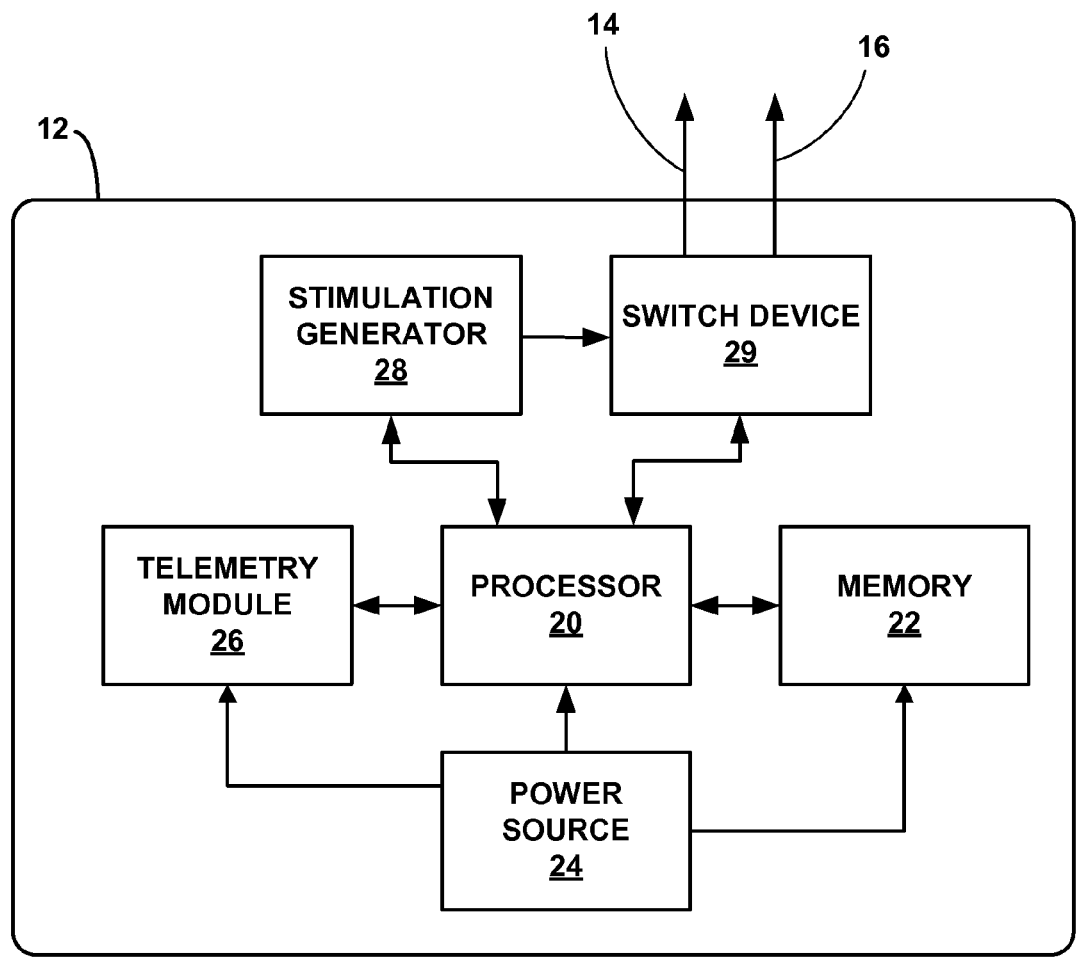
FIG. 2 is a functional block diagram of an example embodiment of the implantable medical device (IMD) of FIG. 1.

FIG. 2 is a functional block diagram of IMD 12 according to one example. In the example illustrated in FIG. 2, IMD 12 includes processor 20, memory 22, power source 24, communication module 26, signal generator 28, and switch device 29. As shown in FIG. 2, switch device 29 is coupled to leads 14 and 16. Alternatively, switch device 29 may be coupled to more than two leads directly or indirectly (e.g., via a lead extension, such as a bifurcating lead extension that may electrically and mechanically coupled to two leads) as needed to provide stimulation therapy to patient 18.

Memory 22 includes computer-readable instructions that, when executed by processor 20, cause IMD 12 and processor 20 to perform various functions attributed to IMD 12 and processor 20 herein. Memory 22 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Stimulation generator 28 produces stimulation signals (e.g., pulses or continuous time signals, such as sine waves) for delivery to patient 18 via selected combinations of electrodes carried by leads 14, 16. Processor 20 controls stimulation generator 28 to apply particular stimulation parameters specified by at least one of programs (e.g., programs stored within memory 22), such as amplitude, pulse width, and pulse rate. Processor 20 may include a microprocessor, a controller, a digital signal processor (DSP), an application specific integrated circuit (ASIC), a field-programmable gate array (FPGA), equivalent discrete or integrated logic circuitry, or any combination of at least one these elements.

Processor 20 also controls switch device 29 to apply the stimulation signals generated by stimulation generator 28 to selected combinations of the electrodes of leads 14, 16 with a polarity, e.g., as specified by at least one stimulation programs or parameters stored in memory 22 and/or received from programmer 19 via communication module 26. In particular, switch device 29 couples stimulation signals generated by stimulation generator 28 to selected conductors within leads 14, 16 which, in turn, delivers the stimulation signals across selected electrodes of leads 14, 16. Switch device 29 may be a switch array, switch matrix, multiplexer, or any other type of switching device suitable to selectively couple stimulation energy to selected electrodes. Hence, stimulation generator 28 is coupled to the electrodes of leads 14, 16 via switch device 29 and conductors within leads 14, 16.

Stimulation generator 28 may be a single- or multi-channel stimulation generator. In particular, stimulation generator 28 may be capable of delivering, a single stimulation pulse, multiple stimulation pulses, or a continuous signal at a given time via a single electrode combination or multiple stimulation pulses at a given time via multiple electrode combinations. In some embodiments, multiple channels of stimulation generator 28 may provide different stimulation signals, e.g., pulses, to different electrodes at substantially the same time. For example, multiple channels of stimulation generator 28 may provide signals with different amplitudes to different electrodes at substantially the same time. Processor 20 may control stimulation generator 28 to generate stimulation in accordance with at least one programs or parameters stored in memory 22 and/or received from programmer 19 via communication module 26. In the case of electrical stimulation pulses, the programs or parameters may specify amplitude, width and rate for pulses generated by stimulation generator 28.

Communication module 26 supports wireless communication between IMD 12 and an external programmer 19 or another computing device under the control of processor 20. In some embodiments, communication module 26 may include a transmitter and receiver to permit bi-directional communication between IMD 12 and programmer 19. Processor 20 of IMD 14 may receive, as updates to programs, values for various stimulation parameters such as amplitude and electrode combination, from programmer 19. The updates to the therapy programs may be stored within memory 22. Additionally, processor 20 may send status and operational information to programmer 19 via communication module 26.

The various components of IMD 12 are coupled to power source 24, which may include a rechargeable or non-rechargeable battery. A non-rechargeable battery may be selected to last for several years, while a rechargeable battery may be inductively charged from an external device, e.g., on a daily or weekly basis. In other embodiments, power source 24 may be powered by proximal inductive interaction with an external power supply carried by patient 18.

Processor 20 may also receive physiological signals sensed by selected electrodes on leads 14, 16 or other leads via switch device 29. In some examples, processor 20 may receive physiological signals sensed by at least one electrode (not shown) located on housing 13 (FIG. 1) of IMD 12, which may be used alone or in combination with lead-borne electrodes for delivery of stimulation or sensing. Furthermore, processor 20 may additionally or alternatively receive at least one signal generated by one or more other sensors 17 that are on or within housing 13, or coupled to processor 20 via a lead or wirelessly, e.g. via communication module 26.

Such physiological signals may include sensing an evoked R-wave or P-wave after delivery of pacing therapy, sensing for the absence of an intrinsic R-wave or P-wave prior to delivering pacing therapy, or detecting a conducted depolarization in an adjacent heart chamber. As with stimulation therapy, selecting which electrode(s) are used for sensing physiological parameters of a patient may alter the signal quality of the sensing techniques. For this reason, sensing techniques may include one or more algorithms to determine the suitability of each electrode or electrode combination in the stimulation therapy system for sensing at least one physiological parameter. Sensing physiological parameters may also be accomplished using electrode or sensors that are separate from the stimulation electrodes, e.g., electrodes capable of delivering stimulation therapy, but not selected to deliver the stimulation therapy that is actually being delivered to the patient.

Figure 3:
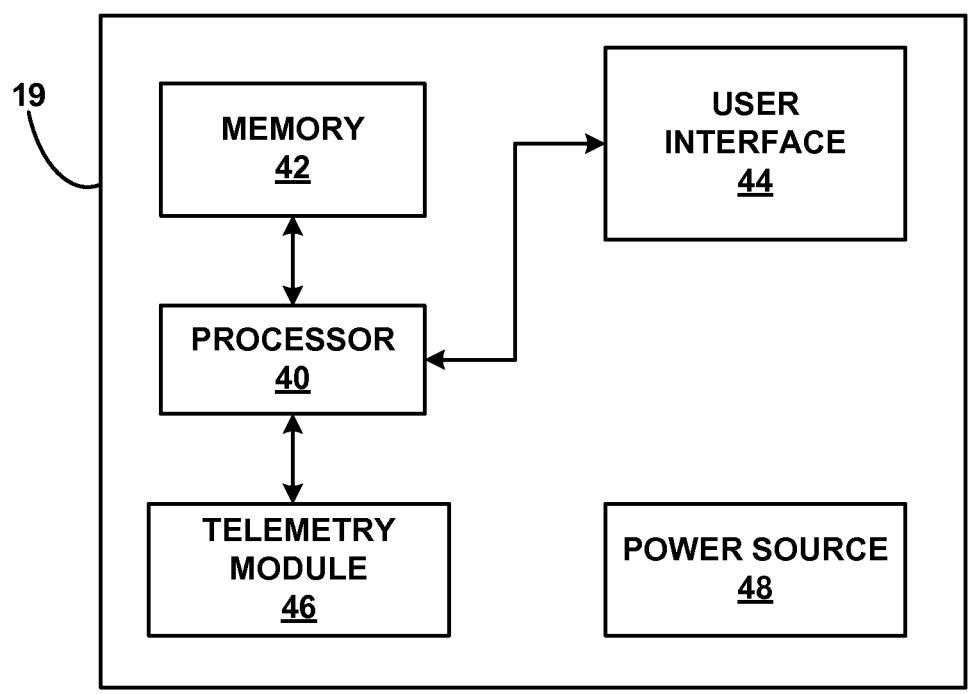
FIG. 3 is a functional block diagram of an example embodiment of the external programmer of FIG. 1.

FIG. 3 is a functional block diagram of an example embodiment of external programmer 19. As shown in FIG. 3, external programmer 19 includes processor 40, memory 42, user interface 44, communication module 46, and power source 48. A clinician or another user may interact with programmer 19 to generate and/or select therapy programs for delivery by IMD 12. For example, in some embodiments, programmer 19 may allow a clinician to define stimulation fields, e.g., select appropriate stimulation parameters for one or more stimulation programs to define the desired stimulation field. Programmer 19 may be used to select stimulation programs, generate new stimulation programs, and transmit the new programs to IMD 12. Processor 40 may store stimulation parameters as one or more stimulation programs in memory 42. Processor 40 may send programs to IMD 12 via communication module 46 to control stimulation automatically and/or as directed by the user.

Programmer 19 may be one of a clinician programmer or a patient programmer, i.e., the programmer may be configured for use depending on the intended user. A clinician programmer may include more functionality than the patient programmer. For example, a clinician programmer may include a more featured user interface, allow a clinician to download therapy usage, sensor, and status information from IMD 12, and allow a clinician to control aspects of IMD 12 not accessible by a patient programmer embodiment of programmer 19.

A user, e.g., a clinician or patient 18, may interact with processor 40 through user interface 44. User interface 44 may include a display, such as a liquid crystal display (LCD), light-emitting diode (LED) display, or other screen, to show information related to stimulation therapy, and buttons or a pad to provide input to programmer 19. Buttons may include an on/off switch, plus and minus buttons to zoom in or out or navigate through options, a select button to pick or store an input, and pointing device, e.g. a mouse, trackball, or stylus. Other input devices may be a wheel to scroll through options or a touch pad to move a pointing device on the display. In some embodiments, the display may be a touch screen that enables the user to select options directly from the display screen.

Programmer 19 may be a handheld computing device, a workstation or another dedicated or multifunction computing device. For example, programmer 19 may be a general purpose computing device (e.g., a personal computer, personal digital assistant (PDA), cell phone, and so forth) or may be a computing device dedicated to programming IMD 12.

Processor 40 processes instructions from memory 42 and may store user input received through user interface 44 into the memory when appropriate for the current therapy. Processor 40 may comprise any at least one of a microprocessor, digital signal processor (DSP), application specific integrated circuit (ASIC), field-programmable gate array (FPGA), or other digital logic circuitry.

Memory 42 may include instructions for operating user interface 44, telemetry module 46, and managing power source 48. Memory 42 may store program instructions that, when executed by processor 40, cause the processor and programmer 19 to provide the functionality ascribed to them herein. Memory 42 may include any at least one of a random access memory (RAM), read-only memory (ROM), electronically-erasable programmable ROM (EEPROM), flash memory, or the like.

Wireless communication in programmer 19, IMD 12 and sensors 17 may be accomplished by radio frequency (RF) communication or proximal inductive interaction of between such devices. This wireless communication is possible in programmer 19 through the use of communication module 46. Accordingly, communication module 46 may include any circuitry known for such communication. For example, communication module 46 may include a transmitter and receiver to permit bi-directional communication between programmer 19 and IMD 12.

Power source 48 delivers operating power to the components of programmer 19. Power source 48 may include a battery and a power generation circuit to produce the operating power. In some embodiments, the battery may be rechargeable to allow extended operation. Recharging may be accomplished through proximal inductive interaction, or electrical contact with circuitry of a base or recharging station. In other embodiments, primary batteries may be used. In addition, programmer 19 may be directly coupled to an alternating current source, such would be the case with some computing devices, such as personal computers.

FIGS. 4-8 illustrate various embodiments of implantable medical leads that may be utilized to deliver, as examples, LV or vagus nerve stimulation. As described in further detail with respect to FIGS. 9 and 10, at least one electrode configuration of one or more of the leads of FIGS. 4-8 may be evaluated to assess myocardial and phrenic nerve capture for LV pacing, or vagus nerve and neck muscle capture for vagus nerve stimulation. Evaluation of myocardial and phrenic nerve capture may help guide selection of an electrode configuration that selectively stimulates the LV without stimulating the phrenic nerve. Similarly, evaluation of vagus nerve and neck muscle capture may help guide selection of an electrode configuration that selectively stimulates the vagus nerve without stimulating the neck muscles.

Figure 4A:
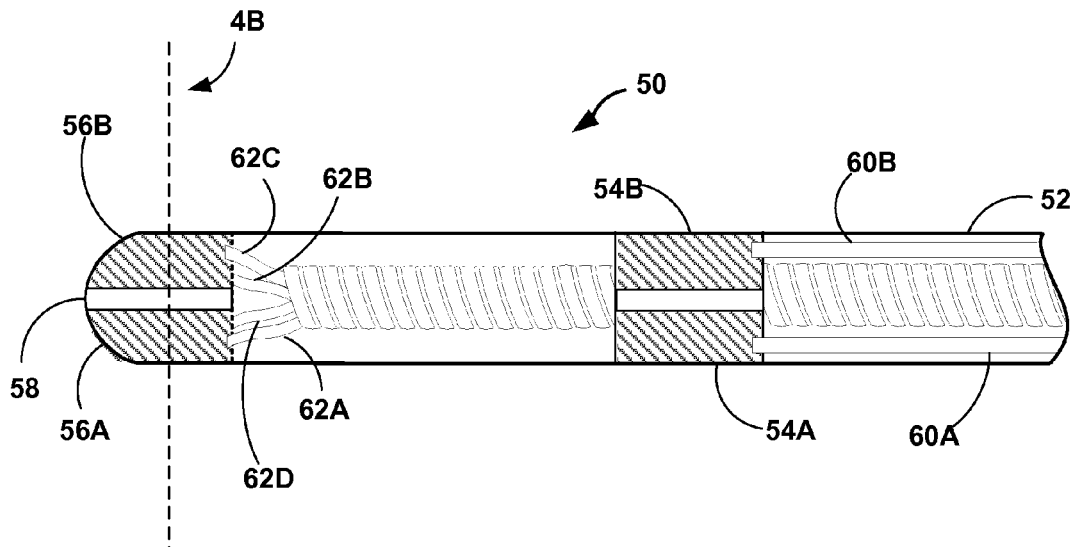
FIG. 4A is a side view of a distal end of an example lead including electrode segments at its distal tip.

FIG. 4A is a side view of a distal end of an embodiment of a lead 50, which may, for example, correspond to either of leads 14, 16 of FIG. 1. A proximal end (not shown) of lead 50 may be coupled to an IMD (e.g., IMD 12 of FIG. 1). Lead 50 includes a lead body 52 and electrodes 54A, 54B, and 56A-56D (electrodes 56C and 56D are not shown in FIG. 4A). Lead body 52 may be formed from a insulative biocompatible material. Exemplary biocompatible material includes at least one covers of polyurethane, silicone, and fluoropolymers such as tetrafluroethylene (ETFE), polytetrafluroethylene (PTFE), and/or expanded PTFE (i.e. porous ePTFE, nonporous ePTFE). Electrodes 54A, 54B, and 56A-56D are exposed to tissue of the patient, which allows data to be sensed from the tissue and/or therapy delivered to the patient.

As shown in FIG. 4A, electrodes 54A and 54B are flush or isodiametric with lead body 22 and may be segmented or partial ring electrodes, each of the electrode segments 54A and 54B extending along an arc less than 360 degrees (e.g., 90-120 degrees). Segmented or partial ring electrodes may be useful for providing an electrical stimulation field that is predominantly focused in a particular transverse direction relative to the longitudinal axis of lead 50, and/or targeting a particular stimulation site. In other embodiments, instead of or in addition to electrodes 54A and 54B, lead 50 may include a ring electrode extending substantially around the entire periphery, e.g., circumference, of lead 50.

Figure 4B:
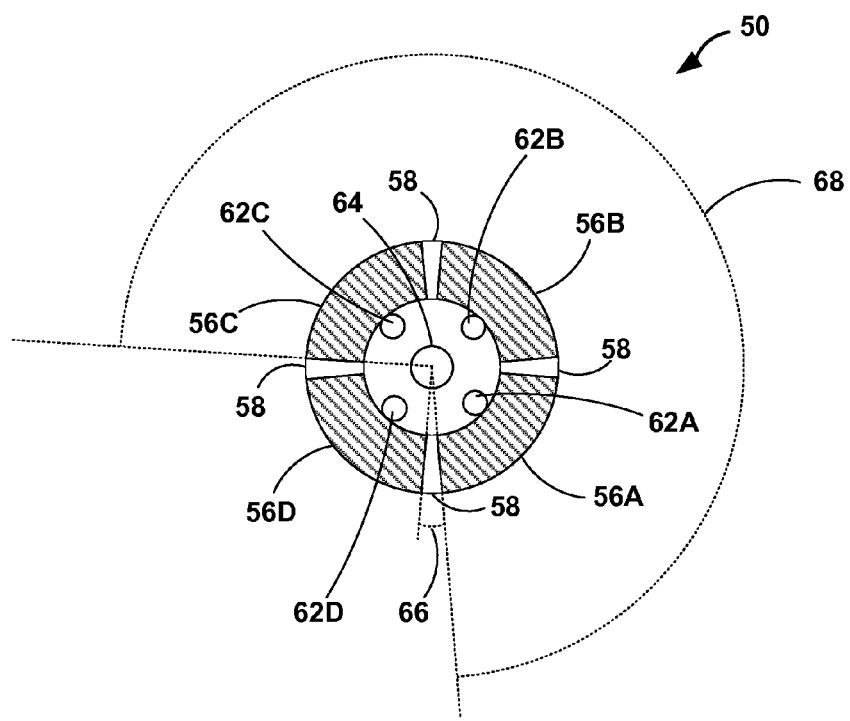
FIGS. 4B-4D are cross-sectional views of the electrode segments at the distal tip the lead of FIG. 4A and an electrical field propagating directionally from the electrode segments.

In the illustrated embodiment, electrodes 56A-56D are also segmented or partial ring electrodes, which do not extend substantially around the entire periphery of the lead body 52. Electrodes 56C and 56D are located on the circumferential portion of lead body 52 not visible in FIG. 4A. As described in further detail below, FIG. 4B is a cross-sectional view of electrodes 56A-56D along line 4B in FIG. 4A, and illustrates the approximate locations of electrodes 56C and 56D. Electrodes 56A-56D may, but need not be, located at the same axial position along the length of lead body 52. When electrodes 56A-56D are located at the same axial position of lead body 52, electrodes 56A-56D may form a row of electrode segments. In some embodiments, electrodes 56A-56D may be evenly spaced around the periphery of lead 50. Additionally, each of individual electrode segments 56A-56D may be separated by insulative material 58, which may aid in electrically isolating each of electrodes 56A-56D.

Each of electrodes 54A, 54B, and 56A-56D can be made from an electrically conductive, biocompatible material, such as platinum iridium. In addition, at least one of electrodes 54A, 54B, and 56A-56D may function as sensing electrodes that monitor internal, physiological, electrical signals of patient 18 (FIG. 1). The configuration, type, and number of electrodes 54A, 54B, and 56A-56D are merely exemplary. In other embodiments, lead 50 may include any configuration, type, and number of electrodes 54A, 54B, and 56A-56D, and is not limited to the embodiment illustrated in FIGS. 4A and 4B.

Within lead body 52, lead 50 also includes insulated electrical conductors 60A and 60B coupled to electrodes 54A and 54B, and insulated electrical conductors 62A-62D coupled to electrode segments 56A-56D, respectively. In the illustrated embodiment, conductors 62A-62D are coiled along the length of lead body 52 (e.g., in a multiconductor coil), and conductors 60A and 60B lie axial to conductors 62A-62D. Conductors 60A and 60 B may or may not be coiled. In the embodiment illustrated in FIG. 4A, each of conductors 60A, 60B, and 62A-62D is electrically coupled to a single one of electrodes 54A, 54B, and 56A-56D, respectively. In this manner, each of electrodes 54A, 54B, and 56A-56D may be independently activated. In other embodiments, a lead including multiple electrodes may include a multiplexer or other switching device such that the lead may include fewer conductors than electrodes, while allowing each of the electrodes to be independently activated. The switching device may be responsive to commands from the IMD or an external source to selectively couple the electrodes to the conductors for delivery of stimulation or for sensing.

The configuration, type, and number of conductors 60A, 60B, and 62A-62D is not limited to the embodiment illustrated in FIG. 4A and, in other embodiments, lead 50 may include any configuration, type, and number of conductors. As one example, in some embodiments, each of conductors 60A, 60B, and 62A-62D may be coiled conductors. Additionally or alternatively, one conductor may be electrically coupled to at least two electrodes.

FIG. 4B is a cross-sectional view electrode segments 56A-56D along line 4B in FIG. 4A. As previously described, each of electrode segments 56A-56D is separated by insulative material 58. The center of lead body 52 may include a lumen 64 to accommodate a delivery device such as a stylet, guidewire or a hybrid of a stylet and guidewire. A delivery device may be used to help position lead 50 at a target location during implantation of lead 50. Electrical conductors 62A-62D are coupled to electrode segments 56A-56D, respectively. Each of conductors 62A-62D extends from electrodes 56A-56D to a proximal end of lead body 52 to couple electrodes 56A-56D to an IMD (e.g., IMD 12 of FIG. 1).

Electrode segments 56A-56D may be useful in directing a stimulation field toward a target site and/or away from a non-target, potentially undesirable, site. For example, at least one of electrode segments 56A-56D may be activated (e.g., as a cathode or an anode) to deliver stimulation to patient 18 (FIG. 1). As will be described in greater detail below, the direction of the stimulation field, e.g., the radial direction relative to the longitudinal axis of elongated lead body 52 or "side" of the lead on which the field is present, may be based on which of electrode segments 56A-56D are activated. Electrodes 54A and 54B may further aid in steering the stimulation field in a particular direction and/or sensing a patient condition on a particular side of lead body 52 Additionally, a current or voltage amplitude may be selected for each of the active electrodes. During movement of lead 20, at least one of the electrodes may produce different amplitudes to further aid in controlling the direction of the stimulation field. All else equal, in a system having two anodes with different amplitudes, each anode adjacent to a cathode, generally, the stimulation field is at least partially biased towards the anode with the higher current or voltage amplitude.

As one example, a directional stimulation field may be particularly useful in LV pacing applications. An IMD (e.g., IMD 12 of FIG. 1) may configure electrodes 54A, 54B, and 56A-56D to direct the stimulation field toward the myocardium and away from the phrenic nerve. More specifically, when lead 50 is transvenously placed proximate to the LV of patient 18 (FIG. 1), it may be desirable to only activate at least one of electrodes 54A, 54B, and 56A-56D positioned proximate to the myocardium (e.g., facing or in contact with the myocardium) rather than those proximate to the epicardium. Selectively activating at least one of electrodes 54A, 54B, and 56A-56C to direct the electrical stimulation field towards the myocardium may reduce the amount of energy required for tissue capture of the myocardium for pacing therapies and, consequently, increase battery life. In addition, directing the electrical stimulation field towards the myocardium may reduce the likelihood of phrenic nerve stimulation, because the electrical stimulation field will generally be directed away from the phrenic nerve. In other words, when the electrical stimulation field is directed toward the myocardium, the excess electrical field directed away from the myocardium and across the pericardium where the phrenic nerve lies that may be present when the electrical stimulation is delivered via a ring electrode that extends substantially completely around the circumference or periphery of a lead may be reduced or eliminated.

A directional stimulation field may be particularly useful when phrenic nerve stimulation occurs post-implant. Using a conventional LV lead, when phrenic nerve stimulation occurs post-implant, the clinician may need to either extract the lead to reposition it or abandon LV pacing. Using a lead with electrode segments, the clinician may alter the electrode configuration to aid in directing the stimulation field away from the phrenic nerve.

As another example, a directional stimulation field may be useful in stimulation of the vagus nerve. Stimulation of the vagus nerve may be performed to decrease heart rate. The vagus nerve is positioned proximate to muscles of the neck, which may inadvertently be stimulated along with the vagus nerve. Controlling the direction of propagation of the stimulation field may aid in preventing stimulation of the neck muscles. As another example, a directional electrical field may be useful in atrial stimulation where it may be desirable to avoid stimulating specific ischemic tissue regions which may result in an arrhythmia. In general, electrodes segments 54A, 54B, and 56A-56D may be useful in any application where controlling the direction of propagation of the stimulation field is desirable.

In one embodiment, the IMD (e.g., IMD 12 of FIG. 1) may configure a first electrode segment as a cathode and two adjacent electrode segments, which may be on opposite sides of the first electrode segment, as anodes. This configuration may be referred to as an "anodal shielding" configuration in the sense that the anodes act as a shield around the cathode to substantially prevent propagation of the electrical field from the cathode to tissue that is beyond the anodes, e.g., tissue on an opposite side of the anode than the cathode.

For example, IMD 12 may configure electrode segment 56B as a cathode and adjacent electrodes segments 56A and 56C on opposite sides of electrode segment 56B as anodes. Electrode segments 56A and 56C (the anodes) may substantially constrain the electrical field propagating from electrode segment 56B (the cathode) to the side or angular section 68 of lead 50 that includes electrode segment 56B. The electrical field may be centered between electrode segments 56A and 56C and, depending on the stimulation amplitudes for each of electrode segments 56A-56C, may be centered substantially over electrode segment 56B. IMD 12 may activate electrode segments 56A-56D in different configurations based on the desired direction of the stimulation field. At least one of electrode segments 54A and 54B may additionally or alternatively be activated as an anode or cathode to aid in controlling the direction of propagation of the stimulation field.

Anodal shielding may limit the size of the stimulation field. For example, the anodes may determine the extent and shape of a volume of tissue to which the stimulation field propagates. In some embodiments, an anodal shielding configuration may prevent the stimulation field from extending past the anodes.

The spacing between each of electrode segments 56A-56D may also influence the size of the stimulation field. In the embodiment illustrated in FIG. 4B, electrodes 56A-56D are evenly or about evenly spaced around the periphery of lead 50 with arc 66 separating each of electrodes 56A-56D. Separation arc 66 may be selected based on the desired size of the stimulation field. In other embodiments, electrode segments 56A-56C may be unevenly spaced around the periphery of lead 50.

Figure 4C:
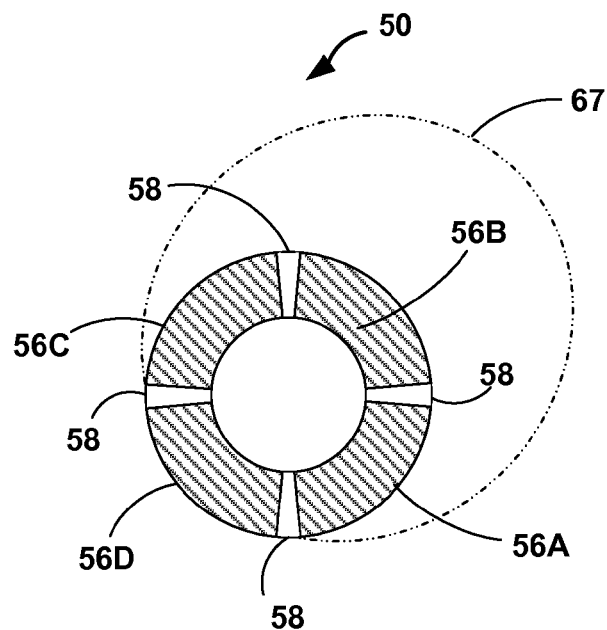

FIG. 4C is another cross-sectional view of electrode segments 56A-56D. FIG. 4C illustrates stimulation field 67 emanating from lead body 52. As described with respect to FIG. 4B, IMD 12 may configure electrode segment 56B as a cathode and adjacent electrodes segments 56A and 56C on opposite sides of electrode segment 56B as anodes. Electrode segments 56A and 56C (the anodes) may substantially constrain stimulation field 67 from propagating past electrode segments 56A and 56C (the anodes). In the embodiment illustrated in FIG. 4C, stimulation field 67 is substantially centered over electrode segment 56B. For example, substantially similar voltage amplitudes may vary by no more than 0.1 volts, and substantially similar current amplitudes may vary by no more than 0.1 milliamps. IMD 12 may activate each of electrode segments 56A-56C with substantially the same amplitude to generate stimulation field 67 substantially centered over electrode segment 56B. IMD 12 may activate electrode segments 56A-56D in different configurations based on the desired direction of the stimulation field.

Figure 4D:
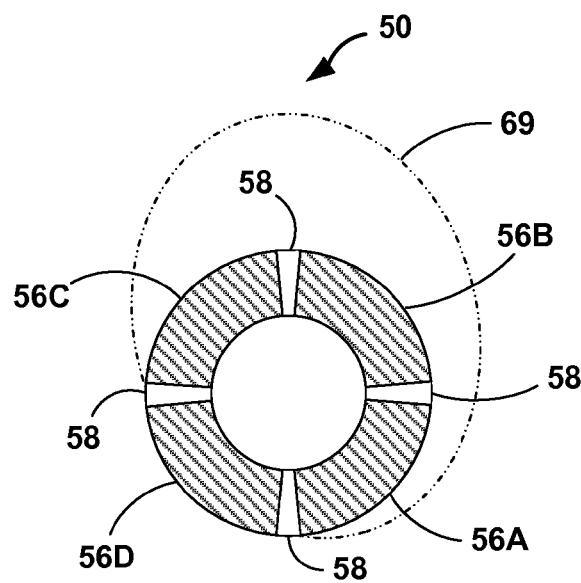

FIG. 4D is another cross-sectional view of electrode segments 56A-56D. FIG. 4D illustrates stimulation field 69 emanating from lead body 52. As described with respect to FIGS. 4B and 4C, IMD 12 may configure electrode segment 56B as a cathode and adjacent electrodes segments 56A and 56C on opposite sides of electrode segment 56B as anodes. Electrode segments 56A and 56C (the anodes) may substantially constrain stimulation field 69 from propagating past electrode segments 56A and 56C (the anodes). In the embodiment illustrated in FIG. 4D, stimulation field 69 is skewed toward electrode 56C compared to stimulation field 67 of FIG. 4C. Rather than being substantially centered over electrode 56B (the central cathode), stimulation field 69 is shifted toward electrode 56C. IMD 12 may activate electrode segments 56A-56C with different current or voltage amplitudes to generate stimulation field 69 shifted toward electrode 56C. Additionally, IMD 12 may activate electrode segments 56A-56D in different configurations based on the desired direction of the stimulation field. For example, IMD 12 may selectively activate two electrode segments 26A-26D a bipolar configuration.

Figure 5A:
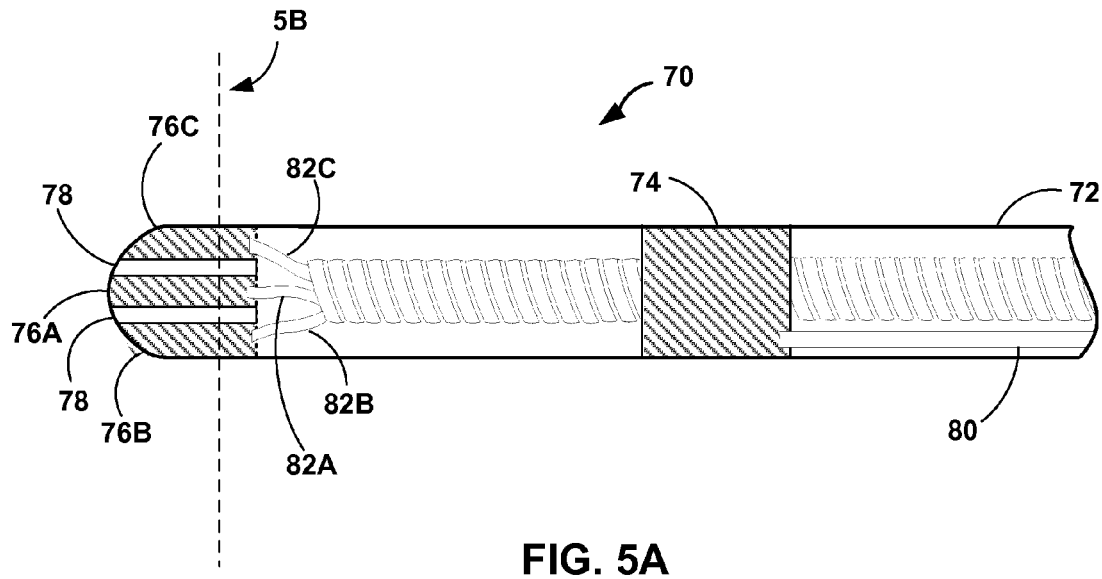
FIG. 5A is a side view of a distal end of another example lead including electrode segments at its distal tip.

FIG. 5A is a side view of a distal end of another embodiment of a lead 70. A proximal end (not shown) of lead 70 may be coupled to an IMD (e.g., IMD 12 of FIG. 1). Lead 70 includes a lead body 72 and electrodes 74 and 76A-76C. An outer surface of lead body 72 may be formed from a biocompatible material such as, for example, polyurethane or silicone. As shown in FIG. 5A, electrode 74 may be a ring electrode extending substantially around the entire periphery, e.g., circumference, of lead 70. In other embodiments, electrode 74 may comprise segmented or partial ring electrodes, each of the electrode segments extending along an arc less than 360 degrees (e.g., 90-120 degrees).

In the illustrated embodiment, electrodes 76A-76C are segmented electrodes, which do not extend substantially around the entire periphery of the lead 70. Electrodes 76A-76C may, but need not be, located at the same axial position along the length of lead body 72. When electrodes 76A-76C are located at the same axial position of lead body 72, electrodes 76A-76C may form a row of electrode segments. In some embodiments, electrodes 76A-76C may be evenly spaced around the periphery of lead 70. Additionally, each of individual electrode segments 76A-76C may be separated by insulative material 78, which may aid in electrically isolating each of electrodes 76A-76C. Insulative material 48 is a biocompatible material having an impedance sufficient to prevent shorting between electrode segments during stimulation therapy. For example, insulative material 48 may comprise polyurethane, silicone, and fluoropolymers such as tetrafluroethylene (ETFE), polytetrafluroethylene (PTFE), and/or expanded PTFE (i.e. porous ePTFE, nonporous ePTFE).

Each of electrodes 74 and 76A-76C can be made from an electrically conductive, biocompatible material, such as platinum iridium. In addition, at least one of electrodes 74 and 76A-76C may function as sensing electrodes that monitor internal physiological signals of patient 18 (FIG. 1). The configuration, type, and number of electrode 74 and 76A-76C are merely exemplary. In other embodiments, lead 70 may include any configuration, type, and number of electrodes 74 and 76A-76C and is not limited to the embodiment illustrated in FIG. 5A.

Electrode segments 76A-76C may be useful in directing a stimulation field toward a target site and/or away from a non-target, potentially undesirable, site. For example, at least one of electrode segments 76A-76C may be activated (e.g., as a cathode or an anode) to deliver stimulation to patient 18 (FIG. 1). The direction of the stimulation field may be based on which electrode segments 76A-76C are activated. A current or voltage amplitude may be selected for each of the active electrodes to further aid in controlling the direction of the stimulation field. Electrodes activated with unequal amplitudes may shift the direction of the stimulation field relative to a central position of a group of active electrodes, e.g., relative to a central cathode, such as described with respect to stimulation field 69 of FIG. 4D. For example, unequal voltage amplitudes may vary by at least 0.1 volts, and unequal current amplitudes may vary by at least 0.1 milliamps.

An IMD (e.g., IMD 12 of FIG. 1) may configure electrode segments 76A-76C in an anodal shielding configuration. For example, IMD 12 may configure electrode segment 76A as a cathode and electrode segments 76B and 76C on opposite sides of electrode segment 76A as anodes. Anodal shielding may limit the size of the stimulation field. For example, the anodes may determine the extent and shape of area that experiences the effect of the stimulation field. In some embodiments, an anodal shielding configuration may prevent the stimulation field from extending past the anodes.

Electrode 74 may allow a conventional electrode configuration, which may be used as an alternative to configurations including electrode segments 76A-76C. Conventionally, a LV lead may utilize a ring electrode as a cathode and the IMD (e.g., IMD 12 of FIG. 1) or a conductive portion (e.g., a coil electrode) on another lead (e.g., a lead with a distal end implanted in the right ventricle) as an anode in a unipolar configuration. As one example, a superior vena cava (SVC) coil and/or a right ventricle (RV) coil of a lead with a distal end implanted in the right ventricle may be activated as an anode. Electrode 74 may activated as cathode in a conventional unipolar configuration. Electrode 74 may provide a clinician with a familiar fall-back configuration.

Lead 70 also includes electrical conductor 80 coupled to electrode 74, and electrical conductors 82A-82C coupled to electrode segments 76A-76C, respectively. In the illustrated embodiment, conductors 82A-82C are coiled along the length of lead body 72 (e.g., in a multiconductor coil), and conductor 80 lies axial to conductors 82A-82C. In the embodiment illustrated in FIG. 5A, each of conductors 80 and 82A-82C is electrically coupled to a single one of electrodes 74 and 76A-76C, respectively. In this manner, each of electrodes 74 and 76A-76C may be independently activated. Electrodes 74 and 76A-76C may be coupled to an IMD (e.g., IMD 12 of FIG. 1) using an industry standard-4 (IS-4) connector, which allows the connection of up to four independently activatable channels. More specifically, conductors 80 and 82A-82C may couple electrodes 74 and 76A-76C to an IMD (e.g., IMD 12 of FIG. 1) via an IS-4 connector. An IS-4 compatible lead may be easily coupled to an IMD configured according to the IS-4 standard.

The configuration, type, and number of conductors 80 and 82A-82C is not limited to the embodiment illustrated in FIG. 5A and, in other embodiments, lead 70 may include any configuration, type, and number of conductors. As one example, in some embodiments, each of conductors 80 and 82A-82C may be coiled conductors. Additionally or alternatively, one conductor may be electrically coupled to at least two electrodes. In other embodiments, lead 70 may include a multiplexer such that lead body 72 may include fewer conductors than electrodes while allowing each of the electrodes to be independently activated.

Figure 5B:
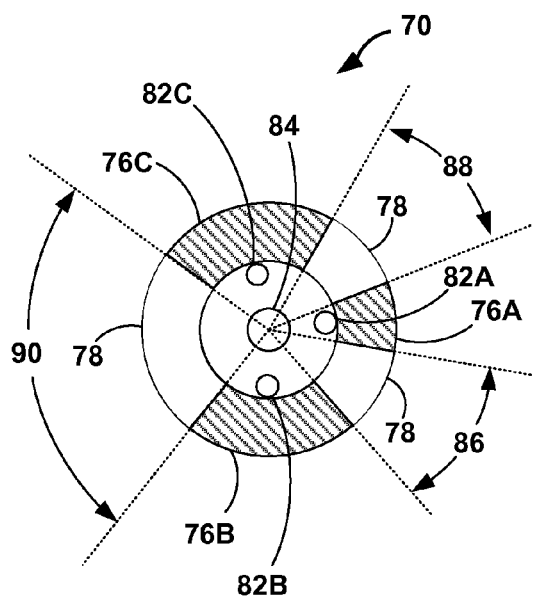
FIG. 5B is a cross-sectional view of the electrode segments at the distal tip the lead of FIG. 5A

FIG. 5B is a cross-sectional view of electrode segments 76A-76C along line 5B in FIG. 5A. As previously described, each of electrode segments 76A-76C is separated by insulative material 78. The center of lead 70 may include a lumen 84 to accommodate a delivery device such as a stylet, guidewire or a hybrid of a stylet and guidewire. A delivery device may be used to help position lead 70 at a target location during implantation of lead 70. Electrical conductors 82A-82C are coupled to electrode segments 76A-76C, respectively. Each of conductors 82A-82C extends from electrodes 76A-76C to a proximal end of lead body 72 to couple electrodes 76A-76C to an IMD (e.g., IMD 12 of FIG. 1).

As described previously, the separation between electrode segments may impact the size of the stimulation field. In the embodiment illustrated in FIG. 5B, electrodes 76A and 76B are separated by arc 86, electrodes 76A and 76C are separated by arc 88, and electrodes 76B and 76C are separated by arc 90. Each of arcs 86, 88, and 90 may extend anywhere from about 1 degree of arc to about 179 degrees of arc. In the embodiment illustrated in FIG. 5B, arcs 86 and 88 are about the same size, and arc 90 is greater than each of arcs 86 and 88.

In some embodiments, electrodes 76A-76C may have different surface areas. For example, the surface area of the anode electrodes may be equal to or larger than the surface area of the cathode electrode. For purposes of example, electrode 76A may be referred to as cathode 76A and electrodes 76B and 76C may be referred to as anodes 76B and 76C. However, electrodes 76A-76C are not limited to this configuration.

In some embodiments, the ratio of the surface area of cathode 76A to the surface area of each of anodes 76B and 76C may range from about 1 to 1 to about 1 to 7. In some embodiments, the ratio of the surface area of cathode 76A to the surface area of each of anodes 76B and 76C may be about 1 to 3. Providing cathode 76A with a smaller surface area than the surface area of each of anodes 76B and 76C may limit anodal corrosion. Additionally, increasing the surface area of each of anodes 76B and 76C may spread the voltage drop out over the surface area of anodes 76B and 76C.

In one embodiment, at least a portion of lead 70, such as electrodes 74 or a separate marker loaded in or formed on lead body 72, may include a radio-opaque material that is detectable by imaging techniques, such as fluoroscopic imaging or x-ray imaging. For example, as described previously, electrodes 74 and 76A-76C may be made of platinum iridium, which is detectable via imaging techniques. This feature may be helpful for maneuvering lead 70 relative to a target site within the body. Radio-opaque markers, as well as other types of markers, such as other types of radiographic and/or visible markers, may also be employed to assist a clinician during the introduction and withdrawal of stimulation lead 70 from a patient. Markers identifying the location of each electrode may be particularly helpful. Since the electrodes rotate with the lead body, a clinician may rotate the lead and the electric field to stimulate a desired tissue. Markers may help guide the rotation.

Figure 6:
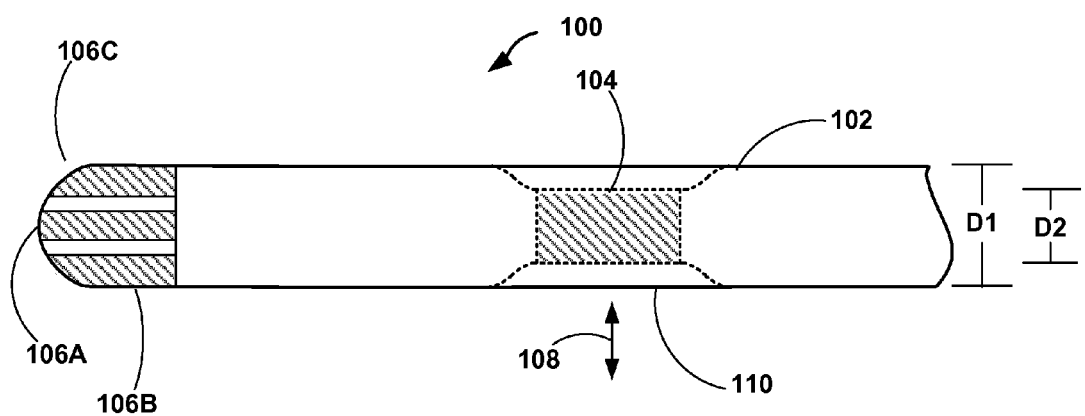
FIG. 6 is a side view of a distal end of an example lead including a recessed electrode.

FIG. 6 is a side view of a distal end of an example lead 100. Lead 100 is substantially similar to lead 70 of FIGS. 5A and 5B but includes a recessed ring electrode 104. Lead 100 includes a lead body 102 and electrodes 104 and 106A-106C. Electrodes 106A-106C may be substantially similar to electrodes 76A-76C of lead 70 and may be arranged in a similar configuration.

Electrode 104 is recessed relative to lead body 102. More particularly, the diameter D2 of electrode 104 is smaller than the diameter D1 of lead body 102 such that electrode 104 is recessed relative to lead body 102. Recessed electrode 104 may aid in limiting the distance a stimulation field extends from an outer diameter of lead body 102 in radial direction 108 perpendicular to the longitudinal axis of lead body 102 relative to an electrode having a diameter D2 equal to diameter D1 of lead body 102. The distance a stimulation field extends from an outer diameter of lead body 102 in radial direction 108 perpendicular to the longitudinal axis of lead body 102 may also be referred to as the depth of the stimulation field. The recessed electrode 104 draws the stimulation field closer to the longitudinal axis of lead body 102. In this manner, the relationship between diameter D2 of electrode 104 and D1 of lead body 102 may aid in controlling the depth of the stimulation field.

Shield 110 is positioned on an outer surface of recessed ring electrode 104 such that shield 110 is substantially flush with lead body 102. This allows lead 100 to be isodiametric throughout the length of lead body 102, which may be helpful in preventing thrombosis. Allowing lead 100 to be isodiametric throughout the length of lead body 102 may also make implantation of lead 100 easier.

Figure 7:
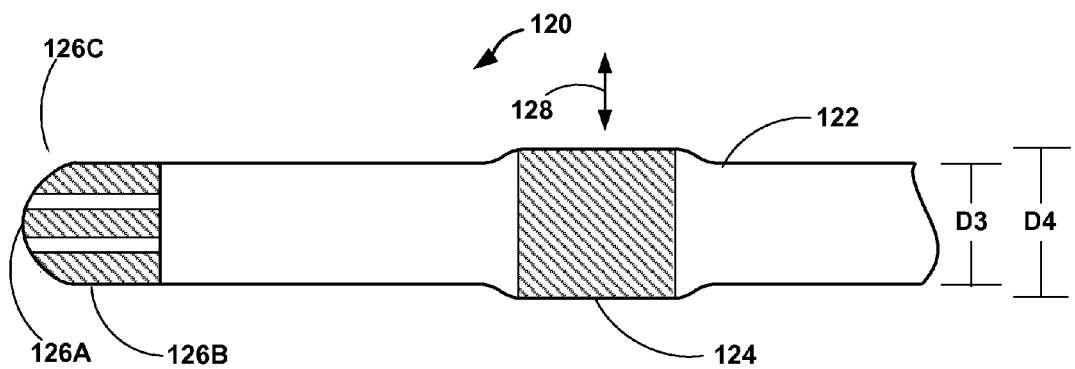
FIG. 7 is a side view of a distal end of an example lead including a protruded electrode.

FIG. 7 is a side view of a distal end of an example lead 120. Like lead 100, lead 120 is also substantially similar to lead 70 of FIGS. 5A and 5B but includes a protruded ring electrode 124. Lead 120 includes a lead body 122 and electrodes 124 and 126A-126C. Electrodes 126A-126C may be substantially similar to electrodes 76A-76C of lead 70 and may be arranged in a similar configuration.

Electrode 124 protrudes relative to lead body 122. More particularly, the diameter D4 of electrode 124 is larger than the diameter D3 of lead body 122 such that electrode 124 protrudes relative to lead body 122. Protruded electrode 124 may aid in increasing the distance a stimulation field extends from an outer diameter of lead body 122 in radial direction 128 perpendicular to the longitudinal axis of lead body 122 relative to an electrode having a diameter D4 equal to diameter D3 of lead body 122. The protruded electrode 124 extends the stimulation field farther from the longitudinal axis of lead body 122. In this manner, the relationship between diameter D4 of electrode 124 and D3 of lead body 122 may aid in controlling the depth of the stimulation field. A stimulation field with increased depth may be useful in delivering stimulation to a target stimulation site further from lead body 122 than reachable if the diameter D4 of electrode 124 equaled the diameter D3 of lead body 122. Recessed and protruded electrodes are described in further detail in commonly-assigned U.S. Utility patent application Ser. No. 12/195,313 by Eggen et al., entitled, "STIMULATION FIELD MANAGEMENT", which was filed on the same date as the present disclosure and is hereby incorporated by reference.

Figure 8:
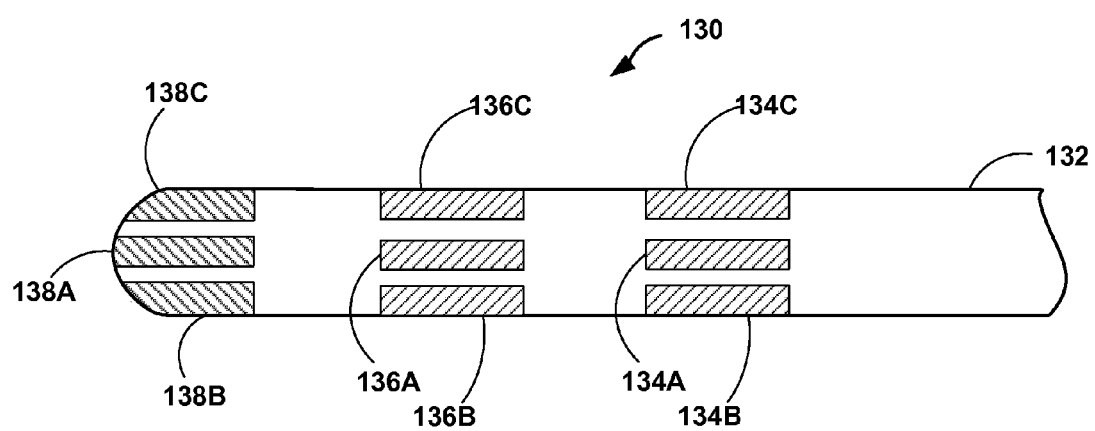
FIG. 8 is a side view of a distal end of another example lead including electrode segments at its distal end.

FIG. 8 is a side view of a distal end of another example lead 130 including electrode segments 134A-134B, 136A-136C and 138A-138C at its distal end. Lead 130 is substantially similar to lead 70 of FIGS. 5A and 5B but includes additional electrode segments 134A-134C and 136A-136C axially displaced from electrode segments 138A-138C. Lead 130 includes a lead body 132 and electrodes 134A-134B, 136A-1360, and 138A-1380.

Electrodes 138A-138C may be substantially similar to electrodes 76A-76C of lead 70 and may be arranged in a similar configuration. For example, a cross-sectional view of electrodes 138A-138C may be substantially similar to the cross-sectional view of electrode 76A-76C illustrated in FIG. 5B. Additionally, both rows of electrode segments 136A-136C and 134A-134C may have cross-sections substantially similar to the embodiment illustrated in FIG. 5B. However, the configuration, number, and type of electrodes illustrated in and described with respect to FIG. 8 are merely exemplary. In other embodiments, lead 130 may include any number of rows of electrode segments, any number of electrode segments per row, and any cross-sectional configuration. Lead 130 may also include electrode segments positioned at various radial and axial positions of lead body 132 such that the electrode segments do not form rows.

An IMD (e.g., IMD 12 of FIG. 1) may configure one of electrode segments 134A-134C, 136A-136C, and 138A-138C as a cathode and two adjacent electrode segments as anodes. As one example, IMD 12 may configure electrode segment 136A as a cathode and electrode segments 136B and 138A as anodes. Electrode segment 136B (the first anode) is located at a radial position adjacent to electrode segment 136A (the cathode) and the same axial position as electrode segment 136A (the cathode). Electrode segment 138A (the second anode) is located at the same radial position as electrode segment 136A (the cathode) and an axial position adjacent to electrode segment 136A (the cathode). In this manner, the electrical field may be constrained from extending beyond electrode segments 136B and 138A (the anodes). For example, the electrical field may not extend transversely outward from the portion of lead body 132 containing electrode segment 136B. Additionally, the electrical field may not extend past electrode segment 138A such that the most distal point of the electrical field may be located at electrode segment 138A. The anode and cathode configuration may be based on the location of a target tissue site and/or a non-target, potentially undesirable, site.

As another example, IMD 12 may configure electrode segment 136A as a cathode and electrode segments 134A and 138A as anodes. Electrode segments 134A and 138A (the anodes) are located at the same radial position as electrode segment 136A (the cathode) and axial positions adjacent to electrode segment 136A (the cathode). In this manner, the electrical field may be constrained from extending beyond electrode segments 134A and 138A (the anodes). For example, the electrical field may not extend more distal than electrode segment 138A or more proximal than electrode segment 134A. Such an anodal shielding configuration may be used to limit the length of the electrical field along the length of lead body 132.

Other anodal shielding configurations may use at least two electrode segments at at least one radial position of lead 130 and at least one axial position of lead 130. For example, in some embodiments, three or more electrode segments 134, 136, 138 at various axial or radial positions relative to a cathode may be activated to substantially surround the cathode, e.g., four more adjacent electrode segments forming a square, diamond, or other geometric shaped "box" around the cathode may be activated as anodes to constrain the resulting electrical field. Any anodal shielding configuration including a cathode and at least two adjacent anodes may be utilized to direct the electrical field toward a target tissue site and/or away from a non-target, potentially undesirable, site.

Figure 9:
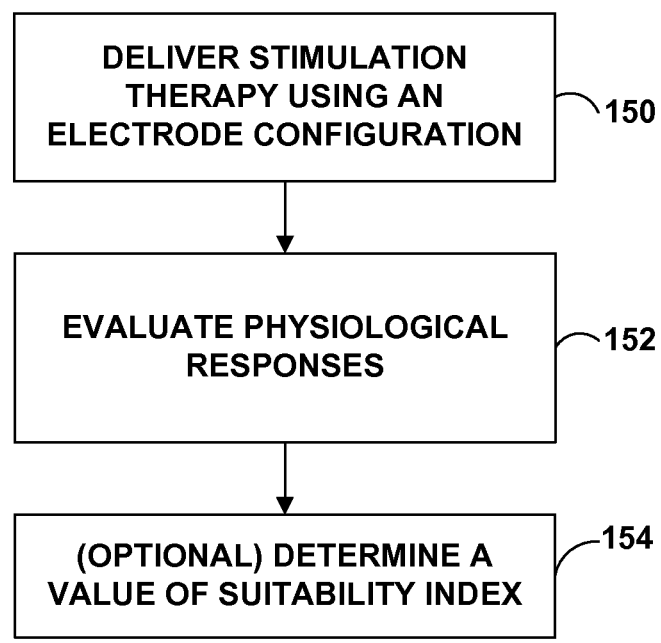
FIG. 9 is a flow diagram illustrating an example technique for evaluating at least one electrode configuration of an implantable medical lead for left ventricle (LV) pacing in a patient.

FIG. 9 is a flowchart illustrating an example technique for evaluating at least one electrode configuration of an implantable medical lead for LV pacing in a patient. While the description of FIG. 9 primarily refers to lead 130 of FIG. 8, in other examples, the techniques for evaluating an electrode configuration may be applied to lead 14, 16, 50, 70, 100, 120, 150, 240 or another lead. While the technique of FIG. 9 is described with respect to processor 20 of IMD 12, it could be performed by either of processor 20 of IMD 12, processor 40 of programmer 19 or both processors 20 and 40 could cooperate to perform the technique. As this example illustrates, a processor as described herein may include more than one processor within more than one device.

Processor 20 controls a switch device to apply the stimulation signals generated by stimulation generator 28 to selected electrodes of lead 130 with specified polarities (150). The activated electrodes and their polarities may be referred to as an electrode configuration. The electrode configuration used for stimulation delivery may be stored in memory 22 of IMD 12 and accessed by processor 20 to control signal generator 28 and switching device 29 accordingly. In some embodiments, processor 40 of programmer 19 may send instructions to IMD 12 that cause processor 20 to access the stored electrode configuration. In other embodiments, rather than storing the electrode configuration in memory 22 of IMD 12, processor 40 of programmer 19 may send the electrode configuration to IMD 12 along with the instructions. In some embodiments, a computer-readable medium, e.g., memory 22 of IMD 12 or memory 42 of programmer 19, may store instructions that cause a processor, e.g., processor 20 of IMD 12 or processor 40 of programmer 19, to perform the functions described with respect to FIG. 9.

To aid in evaluating the electrode configuration, processor 40 of programmer 19 evaluates responses of target tissue and non-target tissue to the stimulation. For example, processor 40 may evaluate capture thresholds, such as both a pacing capture amplitude and a phrenic nerve capture amplitude (152). In some embodiments, the pacing capture amplitude and the phrenic nerve capture amplitude each comprise a voltage amplitude. However, the amplitudes are not limited to voltage amplitudes. For example, at least one of the pacing capture amplitude and the phrenic nerve capture amplitude may comprise a current amplitude. Any therapy parameter used in the therapy directed to the target tissue. For example, a capture threshold may be a stimulation amplitude, stimulation waveform, stimulation pulse width, stimulation pulse frequency, other therapy parameter or a combination of therapy parameters.

Processor 40 of programmer 19 may evaluate each of the pacing capture amplitude and the phrenic nerve capture amplitude by detecting a minimum amplitude (i.e., threshold amplitude) at which capture occurs or determining that capture does not occur at a maximum output. The maximum output may correspond to a maximum output, e.g., voltage or current, that may be produced by signal generator 28 of IMD 12.

The processor may detect pacing capture by monitoring signals from at least one of electrodes 134, 136, 138 (e.g., received via telemetric communication with IMD 12 in the case of processor 40 of programmer 19) or sensor 17 and determining whether the signals indicate LV pacing capture. As one example, sensor 17 may include an oxygen sensor that detects the partial pressure of oxygen in the LV of patient 18. An increased oxygen level in the LV may indicate increased cardiac output and LV pacing capture. An oxygen sensor placed in the pulmonary artery may also generate a signal indicative of cardiac output and, consequentially, LV pacing capture. As another example, processor may receive an electrocardiogram (ECG) signal from at least one of electrodes 134, 136, 138 or sensor 17 and analyze the ECG signal to detect the occurrence of LV pacing capture. Processor 40 may analyze the timing and widths of various waves of the ECG signal and/or the presence of an evoked potential to detect LV pacing capture. As other examples, processor 40 may monitor a heart rate of patient 18 and/or the contractility of heart 5, e.g., via a signal received from an accelerometer.

Processor 40 may, additionally or alternatively, receive user feedback regarding LV pacing capture, e.g., via user interface 44. For example, a clinician may use ultrasound, other imaging techniques, patient feedback, or other evaluative techniques to monitor LV pacing capture. The clinician may alert processor 40 when LV pacing capture occurs via user interface 44.

Similarly, processor may detect phrenic nerve capture based on signals from at least one of electrodes 134, 136, 138 or sensor 17 and/or user feedback received via user interface 44. Since phrenic nerve stimulation may cause hiccups, an accelerometer may be used to detect hiccups and, consequentially, phrenic nerve stimulation. The accelerator may be an external sensor 17 placed on the stomach of patient 18. Alternatively, the accelerator may be implanted within patient 18, e.g., implanted on lead body 132 of lead 130. Movement of lead body 132 may indicate phrenic nerve stimulation. As another example, processor 40 may receive feedback from a user via user interface 44 indicating the occurrence of a hiccup.

To evaluate the capture amplitudes, processor 20 of IMD 12 may iteratively and/or automatically increase a voltage or current amplitude of the stimulation signal until both pacing and phrenic nerve capture are detected. The amplitude at which capture is first detected may be recorded for both pacing and phrenic nerve capture. If the amplitude of the stimulation signal is increased to the maximum output that IMD 12 can support without pacing and/or phrenic nerve capture, a no capture indication may be recorded for the pacing and/or phrenic nerve amplitude.

In some embodiments, processor 20 may present the results of the pacing and phrenic nerve capture evaluation to a user, e.g., via user interface 44 of programmer 19. The user may select at least one electrode combinations based on the displayed results.

A suitability index value may optionally be determined for the electrode configuration based on the evaluation of the pacing and phrenic nerve capture amplitudes (154). In some embodiments, the processor may determine the suitability index value based on the results of the pacing and phrenic nerve capture amplitude evaluation. In other embodiments, the results may be sent to programmer 19, and processor 40 of programmer 19 may determine the suitability index value.

As one example, the suitability index value may be the ratio of the phrenic nerve capture amplitude to the pacing capture amplitude. When a plurality of electrode configurations are evaluated, suitability index values for each of the electrode configurations may be easily compared. The suitability index value may be presented to a user, e.g., via user interface 44 of programmer 19 in addition to or as an alternative to displaying the results of the pacing and phrenic nerve capture evaluation.

Figure 10:
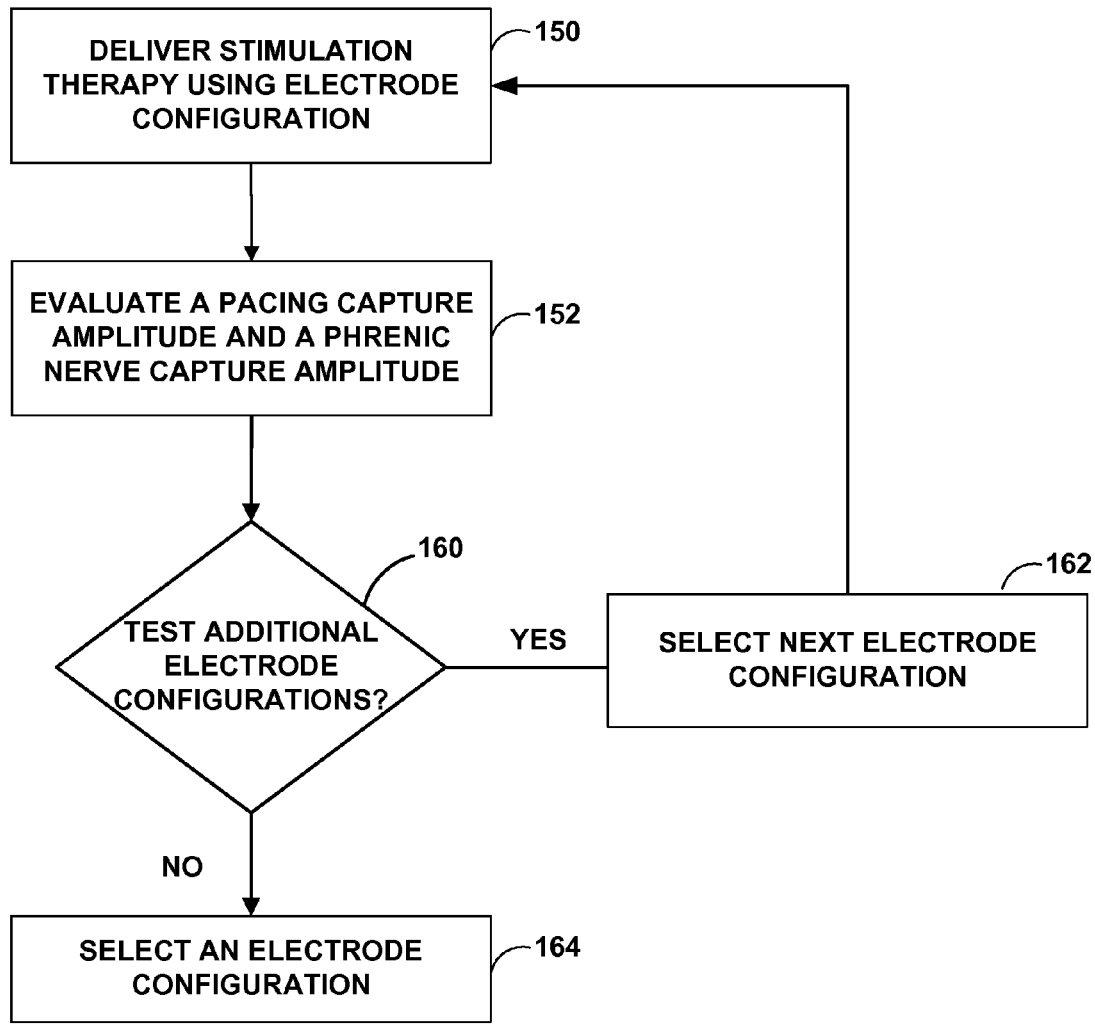
FIG. 10 is a flow diagram illustrating an example technique for evaluating a plurality of electrode configurations for LV pacing in a patient.

As mentioned previously, a plurality of electrode configurations may be evaluated. FIG. 10 is a flowchart illustrating an example technique for evaluating a plurality of electrode configurations for LV pacing in a patient. In some embodiments, a computer-readable medium, e.g., memory 22 of IMD 12 or memory 42 of programmer 19, may store instructions that cause a processor, e.g., processor 20 of IMD 12 or processor 40 of programmer 19, to perform the functions described with respect to FIG. 9. As previously described with respect to FIG. 9, processor 20 controls switch device 29 to apply the stimulation signals generated by stimulation generator 28 to a specific electrode configuration of lead 130 (150), and both a pacing capture amplitude and a phrenic nerve capture amplitude are evaluated (152).

If additional electrode configurations are to be tested (160), the next electrode configuration is selected (162). For example, a user may analyze the results of the pacing and phrenic nerve capture amplitude evaluation and/or a suitability index value via programmer 19 and chose which, if any, electrode configuration to test next. As another example, a list of electrode configuration to test may be predetermined. The list may include electrode configurations chosen by a clinician and selecting the next electrode combination may comprise selecting the next electrode configuration on the list until all of the listed combinations have been tested. As yet another embodiment, a processor, e.g., processor 20 of IMD 12 or processor 40 of programmer 19, may analyze the results of the pacing and phrenic nerve capture amplitude evaluation and/or a suitability index value and chose which, if any, electrode configuration to test next.

If no additional electrode configurations are to be tested (160), at least one electrode configuration may be selected for LV pacing (164). A user of programmer 19, processor 20 of IMD 12, and/or processor 40 of programmer 19 may facilitate the selection. As one example, programmer 19 displays results of the capture evaluation for each electrode configurations, and a user makes a selection using user interface 44 of programmer 19.

In some embodiments, the selection may be at least partially based on suitability index values. As described previously, the suitability index value may be the ratio of the phrenic nerve capture amplitude to the pacing capture amplitude. When a plurality of electrode configurations are evaluated, suitability index values for each of the electrode configurations may be easily compared.

In addition to suitability index values, the selection may be based on the pacing capture amplitude values. A low pacing capture amplitude may permit therapy delivery with a low amplitude, which may subsequently reduce power consumption and increase battery life. In one example procedure, a processor, e.g., processor 20 of IMD 12 or processor 40 of programmer 19, may first compare the suitability index values to a threshold value and then evaluate the pacing capture amplitude values for a subset of electrode configurations. For example, the processor may compare each of the suitability index values to a threshold value and eliminate electrode configurations with suitability index values below the threshold value from consideration. The threshold value may be clinician-specific and may be entered using user interface 44 of programmer 19. As one example the threshold comparison may specify that the phrenic nerve capture amplitude must be at least two times greater than the pacing capture amplitude. The electrode configurations with suitability index values that meet this criterion may be further evaluated based on pacing capture amplitude values.

The processes described above with respect FIGS. 9 and 10 may alternatively be applied to evaluating at least one electrode configuration of an implantable medical lead for vagus nerve stimulation. Instead of evaluating pacing capture and phrenic nerve capture amplitudes as described with respect to LV pacing, vagus nerve capture and muscle capture amplitudes may be evaluated. As described previously, it may be desirable to selectively stimulate the vagus nerve without stimulating the muscle tissue proximate to the vagus nerve. Stimulation of the muscle tissue of the neck may cause undesirable muscle contraction. An example suitability index value for vagus nerve stimulation may be the ratio of the muscle capture amplitude to the vagus nerve capture amplitude.

Like LV pacing and phrenic nerve capture, each of vagus nerve capture and neck muscle capture may be detected based on signals from at least one of electrodes 134, 136, 138 or sensor 17 and/or user feedback received via user interface 44. As one example, an accelerometer implanted within or external to the neck of patient 18 may detect contraction of the neck muscles caused by capture of those muscles. As another example, a user may provide feedback indicating the occurrence of neck muscle contraction via user interface 44. Vagus nerve capture, for example, may be detected based on the heart rate of patient 18, since stimulation of the vagus nerve may cause a decrease in heart rate.

Figure 11:
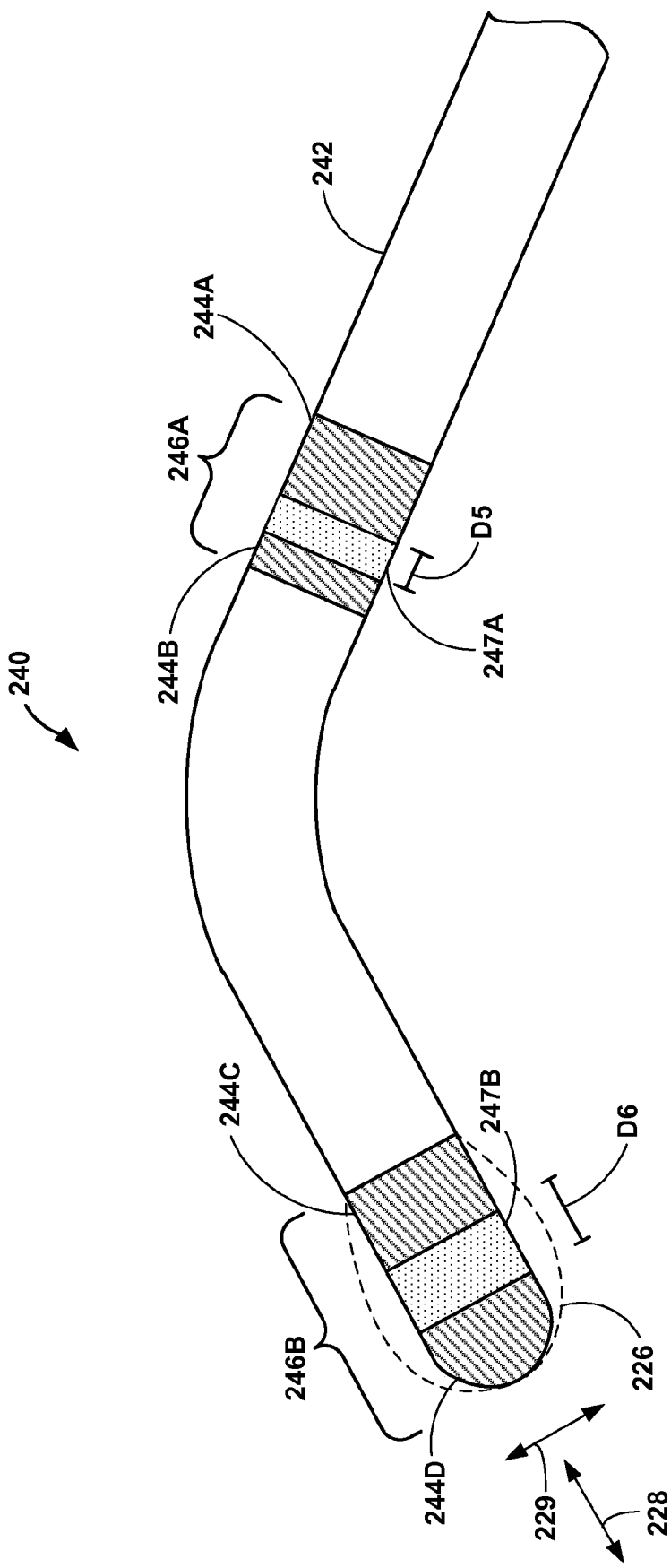
FIG. 11 is a side view of a distal end of an example lead including two pairs of closely spaced electrodes.

FIG. 11 is a side view of an embodiment of a distal end of a lead 240, which may, for example, correspond to either of leads 14, 16 of FIG. 1. Lead 240 includes four electrodes 244A-244D (collectively "electrodes 244"). Lead 240 includes a lead body 242 that extends from a proximal end (not shown) to a distal end that includes electrodes 244. Lead 240 may coupled to an IMD (e.g., IMD 12 of FIG. 1) or other device including a stimulation generator. Lead body 242 may be sized to fit in a small and/or large coronary vein. Accordingly, electrodes 244 may also be sized based on the size of lead body 242 and a target stimulation site within a patient (e.g., patient 18 of FIG. 1).

In some embodiments, at least one of electrodes 244 may be ring electrodes, each with a substantially circular cross-section. In other embodiments, electrodes 244 may comprise segmented or partial ring electrodes. In the embodiment illustrated in FIG. 11, electrodes 244 may be coupled to a device including a stimulation generator using an IS-4 connector, which allows the connection of up to four independently activatable channels. More specifically, conductors (not shown) may couple electrodes 244 to a device including a stimulation generator via an IS-4 connector. In other embodiments, lead 240 may include any configuration, type, and number of electrodes 244 and is not limited to the embodiment illustrated in FIG. 11.

In the embodiment illustrated in FIG. 11, electrodes 244 are axially displaced from one another along the length of lead body 242. Additionally, electrodes 244 are arranged in two pairs of closely spaced electrodes. For example, electrodes 244A and 244B comprise a first pair 246A, and electrodes 244C and 244D comprise a second pair 246B. Additionally, lead 240 may also include monolithic controlled release device (MCRD) 247A containing a steroid between electrodes 244A and 244B of pair 246A and MCRD 247B containing a steroid between electrodes 244C and 244D of pair 246B. One of electrodes 244 in one of pairs 246 may be configured as a cathode and the other electrode of the same pair may be configured as an anode. This configuration may be referred to as a bipolar mode. The other pair 246 may be activated in a similar manner. The two pairs 246 of electrodes 244 may allow an IMD (e.g., IMD 12 of FIG. 1) to deliver a stimulation signal to two different sites corresponding to the locations of pairs 246. Pairs 246 may be activated individually and/or simultaneously. For example, a clinician may be allowed to switch between pairs 246 (e.g., via programmer 19 of FIG. 1) if one of pairs 246 is or becomes less optimal.

The distance D5 between electrodes 244A and 244B of pair 246A may be limited to help control the size of the stimulation field. The distance D6 between electrodes 244C and 244D of pair 246B may also be limited in a similar manner. Limiting distances D5 and D6 may provide a voltage drop to the anode and reduce the size of the electrical field compared to a lead with larger spacing between the cathode and anode.

The short cathode to anode spacing D5 and D6 may be useful in preventing undesirable stimulation of nerves and/or muscles outside the proximity of lead body 242. As one example, a field of limited size may be particularly useful in LV pacing applications. The short cathode to anode spacing D5 and D6 may allow placement of a LV lead to be performed with minimal chance of stimulating the phrenic nerve. Since the electrical field created using a closely spaced cathode and anode in a bipolar mode is limited in size, the electrical field may be prevented from reaching the phrenic nerve. Providing two pairs 46 of electrodes 44 may allow dual stimulation of two stimulation sites while avoiding phrenic nerve stimulation.

A stimulation field limited in size may also be useful for other applications. As one example, a limited electrical field may be useful in stimulation of the vagus nerve. Stimulation of the vagus nerve may be performed to decrease heart rate. The vagus nerve is positioned proximate to muscles of the neck, which may inadvertently be stimulated along with the vagus nerve. Controlling the depth of the stimulation field may aid in preventing stimulation of the neck muscles. As another example, an electrical field of limited size may be useful in atrial stimulation where it may be desirable to avoid stimulating specific ischemic tissue regions. In general, close anode to cathode spacing may be beneficial in any application where controlling the reach of the stimulation field is desirable.

As one example, when electrode 244D is configured as a cathode and electrode 244C is configured as an anode, outline 226 may represent the outer boundaries of the stimulation field. In contrast, using the same anode and cathode configuration but increasing the distance D6 between electrodes 244C and 244D would generally increase the size of the stimulation field along the longitudinal axis of lead body 242 in direction 228 and increase the depth of the stimulation field in direction 229 perpendicular to the longitudinal axis of lead body 242. The close anode to cathode spacing D6 may limit the length of the stimulation field along the longitudinal axis of lead body 242 and/or the depth of the stimulation field perpendicular to the longitudinal axis of lead body 242. In this manner, the anode to cathode spacing D6 may be selected to aid in selectively exciting a tissue based on the geometrical proximity to lead 240 and/or the field gradient to which the tissue responds.

Each of distances D5 and D6 may be less than about 10 mm. For example, in some embodiments, the cathode to anode spacing D5 and D6 may be between about 0.254 mm and about 6.35 mm. Further, in some embodiments, the cathode to anode spacing D5 and D6 may be about 1 mm.

In some embodiments, the surface area of the anode electrode may be equal to or larger than the surface area of the cathode electrode. For purposes of example, electrode 44B may be referred to as cathode 244B and electrode 244A may be referred to as anode 244A. However, electrodes 244A and 244B are not limited to this configuration. For example, the position of the cathode and anode within electrode pair 246A may be switched. Additionally, electrodes 244C and 244D of electrode pair 246B may have a similar configuration to that of electrode pair 246A.

In some embodiments, the ratio of the surface area of cathode 244B to the surface area of anode 244A may range from about 1 to 1 to about 1 to 7. In some embodiments, the ratio of the surface area of cathode 244B to the surface area of anode 44A may be about 1 to 3. As one example, the surface area of cathode 244B may be about 2 mm$^2$, and the surface area of anode 44A may be about 6 mm$^2$. In another embodiment, the surface area of cathode 244B may be about 5 mm$^2$, and the surface area of anode 44A may be about 15 mm$^2$. Providing cathode 244B with a smaller surface area than the surface area of anode 244A may limit anodal corrosion. Additionally, increasing the surface area of anode 244A spreads the voltage drop out over the surface area of anode 244A.

Lead 240 may be used as part of a medical system that provides automated evaluation of a plurality of lead electrode configurations. For example, different electrode configurations using lead 240 include not only bipolar configurations using one of electrode pairs 246B configured to include an anode and a cathode, but also using a different combination of electrodes 244 as anodes and/or cathodes and even using any of electrodes 244 as unipolar electrodes.

The spacing and number of ring electrodes in lead 240 is merely exemplary. Leads having any number of ring electrodes at different axial positions of lead may be used as part of a medical system that provides automated evaluation of a plurality of lead electrode configurations.

Various embodiments have been described. However, modifications may be made to the described embodiments within the spirit of the present disclosure. For example, leads used in conjunction with the techniques described herein may include fixation mechanisms, such as tines that passively secure a lead in an implanted position or a helix located at a distal end of the lead that requires rotation of the lead during implantation to secure the helix to a body tissue.

As another example, although described herein as being coupled to IMDs, implantable medical leads of according to the present disclosure may also be percutaneously coupled to an external medical device for deliver of electrical stimulation to target locations within the patient.

These and other embodiments are within the scope of the following claims.

The invention claimed is:

1. A medical device comprising:
   a means for delivering stimulation therapy to a patient using a plurality of electrode configurations;
   a means for determining a response of a target tissue for each of the plurality of electrode configurations;
   an accelerometer that outputs a signal corresponding to a response of non-target tissue for each of the plurality of electrode configurations;
   a means for evaluating the response of the target tissue and the signal corresponding to the response of the non-target tissue for each of the plurality of electrode configurations to determine the relative suitability of the electrode configurations for delivering stimulation therapy to target tissue of the patient; and
   a means for presenting an indication of the relative suitability of the of the electrode configurations to a use;
   at least one implantable medical lead, wherein the at least one implantable medical lead includes a plurality of electrodes providing the plurality of electrode configurations; and
   wherein the at least one implantable medical lead comprises a cardiac pacing lead, wherein the target tissue comprises tissue of the left ventricle of the patient and the non-target tissue comprises tissue of the phrenic nerve of the patient.

2. The device of claim 1, wherein the means for delivering stimulation therapy comprises an implantable pulse generator.

3. The device of claim 2, wherein the means for evaluating comprises a processor which controls the implantable pulse generator to deliver the stimulation to the patient using the plurality of electrode configurations.

4. The device of claim 2, wherein means for presenting an indication comprises an external programmer.

5. The device of claim 1, wherein the first response of target tissue comprises a first capture threshold of target tissue and the second response of non-target tissue comprises a second capture threshold of non-target tissue.

6. The device of claim 5, wherein determining the first and second responses for the electrode configurations includes determining that at least one of the first and second capture thresholds exceeds a maximum stimulation amplitude allowed by the medical system.

7. The device of claim 5, wherein selecting at least one of the electrode configurations for delivery of stimulation to the patient based on the first and second responses for the electrode configurations includes determining a value of a suitability index for each of the electrode configurations based on a ratio of the first second capture threshold to the second capture threshold for each of the electrode configurations.

8. A medical device comprising:
   a means for delivering stimulation therapy to a patient using a plurality of electrode configurations;
   a means for determining a response of a target tissue for each of the plurality of electrode configurations;
   an accelerometer that outputs a signal corresponding to a response of non-target tissue for each of the plurality of electrode configurations;
   a means for evaluating the response of the target tissue and the signal corresponding to the response of the non-target tissue for each of the plurality of electrode configurations to determine the relative suitability of the electrode configurations for delivering stimulation therapy to target tissue of the patient; and
   a means for presenting an indication of the relative suitability of the of the electrode configurations to a use;
   at least one implantable medical lead, wherein the at least one implantable medical lead includes a plurality of electrodes providing the plurality of electrode configurations; and
   wherein the target tissue comprises tissue of the vagus nerve of the patient and the non-target tissue comprises muscle tissue of the patient adjacent to the vagus nerve.

9. A medical system comprising:
   one or more implantable medical leads, the implantable medical leads including a plurality of electrodes;
   one or more sensors configured to output one or more signals based on at least one physiological parameter of a patient; and
   a processor configured to:
      control delivery of stimulation to the patient using a plurality of electrode configurations, wherein each of the electrode configurations comprises at least one of the plurality of electrodes,
      for each of the electrode configurations, determine a first response of the left ventricle of the patient to the stimulation based on the signals and a second response of tissue of the phrenic nerve of the patient to the stimulation based on the signals, wherein the processor determines the second response of tissue of the phrenic nerve using an input from an accelerometer, and present indications of the first response of the left ventricle of the patient to the stimulation and the second response of tissue of the phrenic nerve of the patient to a user via a user interface.

10. The system of claim 9, wherein the first response of target tissue comprises a first capture threshold of target tissue and the second response of non-target tissue comprises a second capture threshold of non-target tissue.

11. The system of claim 10, wherein determining the first and second responses for the electrode configurations includes determining that at least one of the first and second capture thresholds exceeds a maximum stimulation amplitude allowed by the medical system.

12. The system of claim 10, wherein selecting at least one of the electrode configurations for delivery of stimulation to the patient based on the first and second responses for the electrode configurations includes determining a value of a suitability index for each of the electrode configurations based on a ratio of the first second capture threshold to the second capture threshold for each of the electrode configurations.

13. A medical system comprising:
one or more implantable medical leads, the implantable medical leads including a plurality of electrodes;
one or more sensors configured to output one or more signals based on at least one physiological parameter of a patient; and
a processor configured to:
control delivery of stimulation to the patient using a plurality of electrode configurations, wherein each of the electrode configurations comprises at least one of the plurality of electrodes,
for each of the electrode configurations, determine a first response of the vagus nerve of the patient to the stimulation based on the signals, and a second response of muscle tissue of the patient adjacent to the vagus nerve to the stimulation based on the signals, wherein the processor determines the second response of the muscle tissue of the patient adjacent to the vagus nerve using an input from an accelerometer, and
present indications of the first response of the vagus nerve of the patient to the stimulation and the second response of the muscle tissue of the patient adjacent to the vagus nerve to a user via a user interface.

14. The system of claim 13, wherein the first response of target tissue comprises a first capture threshold of target tissue and the second response of non-target tissue comprises a second capture threshold of non-target tissue.

15. The system of claim 14, wherein determining the first and second responses for the electrode configurations includes determining that at least one of the first and second capture thresholds exceeds a maximum stimulation amplitude allowed by the medical system.

16. The system of claim 14, wherein selecting at least one of the electrode configurations for delivery of stimulation to the patient based on the first and second responses for the electrode configurations includes determining a value of a suitability index for each of the electrode configurations based on a ratio of the first second capture threshold to the second capture threshold for each of the electrode configurations.

* * * * *